US011647334B2

United States Patent
Yoshida et al.

(10) Patent No.: US 11,647,334 B2
(45) Date of Patent: May 9, 2023

(54) INFORMATION PROCESSING APPARATUS, INFORMATION PROCESSING METHOD, AND VIDEO SOUND OUTPUT SYSTEM

(71) Applicant: Sony Group Corporation, Tokyo (JP)

(72) Inventors: Akira Yoshida, Tokyo (JP); Hiroshi Adachi, Tokyo (JP); Naoki Okamoto, Tokyo (JP)

(73) Assignee: Sony Group Corporation

( * ) Notice: Subject to any disclaimer, the term of this patent is extended or adjusted under 35 U.S.C. 154(b) by 0 days.

(21) Appl. No.: 17/265,621

(22) PCT Filed: Jul. 24, 2019

(86) PCT No.: PCT/JP2019/028972
§ 371 (c)(1),
(2) Date: Feb. 3, 2021

(87) PCT Pub. No.: WO2020/031696
PCT Pub. Date: Feb. 13, 2020

(65) Prior Publication Data
US 2021/0306752 A1 Sep. 30, 2021

(30) Foreign Application Priority Data

Aug. 10, 2018 (JP) .............................. JP2018-152121
May 17, 2019 (WO) .................. PCT/JP2019/019714

(51) Int. Cl.
*H04R 5/04* (2006.01)
*H04R 1/40* (2006.01)
(Continued)

(52) U.S. Cl.
CPC ............... *H04R 5/04* (2013.01); *H04R 1/406* (2013.01); *H04R 5/02* (2013.01); *H04S 7/302* (2013.01); *H04S 7/40* (2013.01)

(58) Field of Classification Search
CPC ............ H04S 7/30; H04S 2400/11; H04S 7/40
(Continued)

(56) References Cited

U.S. PATENT DOCUMENTS

2004/0139480 A1\* 7/2004 Delpuch ............ H04N 7/17318
348/E7.071
2009/0154896 A1 6/2009 Matono
(Continued)

FOREIGN PATENT DOCUMENTS

| CN | 1498035 A | 5/2004 |
| CN | 1750605 A | 3/2006 |

(Continued)

OTHER PUBLICATIONS

International Search Report for Application No. PCT/JP2019/028972 dated Sep. 24, 2019, 3 pages.
(Continued)

*Primary Examiner* — Alexander Krzystan
(74) *Attorney, Agent, or Firm* — Lerner David LLP

(57) ABSTRACT

The information processing apparatus includes a control section that detects a position of a sound source appearing in a video displayed on a screen of a display unit and that uses one or more vibrators to vibrate the display unit and thereby control output of sound such that a sound image of sound in synchronization with the video is localized at the position where the sound source appears on the screen displaying the video. In a case of displaying videos of two or more video sources on individual windows, the control section localizes a sound image of a sound source detected from the video of each video source at a position where the sound source appears in the corresponding window.

12 Claims, 24 Drawing Sheets

(51) Int. Cl.
*H04R 5/02* (2006.01)
*H04S 7/00* (2006.01)

(58) Field of Classification Search
USPC .................................. 700/94; 381/306, 310
See application file for complete search history.

(56) References Cited

U.S. PATENT DOCUMENTS

| | | | |
|---|---|---|---|
| 2010/0014719 A1 | 1/2010 | Date et al. | |
| 2010/0328419 A1 | 12/2010 | Etter | |
| 2011/0001763 A1 | 1/2011 | Murakami | |
| 2012/0002024 A1* | 1/2012 | Choi | H04N 5/60 348/54 |
| 2013/0163952 A1 | 6/2013 | Ni et al. | |
| 2014/0241558 A1* | 8/2014 | Yliaho | H04R 5/02 381/333 |
| 2016/0111096 A1* | 4/2016 | Oh | H04S 7/308 381/22 |
| 2016/0198097 A1* | 7/2016 | Yewdall | H04N 5/272 348/659 |
| 2017/0127209 A1 | 5/2017 | Bostick | |
| 2019/0200097 A1* | 6/2019 | Lee | H04N 21/6125 |

FOREIGN PATENT DOCUMENTS

| | | |
|---|---|---|
| CN | 104714734 A | 6/2015 |
| CN | 105892651 A | 8/2016 |
| EP | 2270772 A2 | 1/2011 |
| GB | 2534165 A | 7/2016 |
| JP | 3526056 B2 | 5/2004 |
| JP | 2004187288 A | 7/2004 |
| JP | 2010206265 A | 9/2010 |
| JP | 2011259299 A | 12/2011 |
| JP | 2013031046 A | 2/2013 |
| JP | 2013102389 A | 5/2013 |
| WO | 2005057549 A1 | 6/2005 |
| WO | 2010035477 A1 | 4/2010 |
| WO | 2012029790 A1 | 3/2012 |
| WO | 2017091509 A1 | 6/2017 |
| WO | 2017098772 A1 | 6/2017 |

OTHER PUBLICATIONS

Hu Yongtao Herohuyongtao@gmail.com et al: "Speaker-Following Video Subtitles", ACM Transactions on Multimedia Computing Communications And Applications, Association for Computing Machinery, US, vol. 11, No. 2, Jan. 7, 2015 (Jan. 7, 2015), pp. 1-17, XP0585170002, ISSN: 1551-6857, DOI: 10.1145/2632111.
Communication pursuant to Article 94(3) EPC for Application No. 19 846 669.0 dated Sep. 6, 2022, 6 pgs.

* cited by examiner

INFORMATION PROCESSING APPARATUS, INFORMATION PROCESSING METHOD, AND VIDEO SOUND OUTPUT SYSTEM

CROSS-REFERENCE TO RELATED APPLICATIONS

This application is a national phase entry under 35 U.S.C. § 371 of International Application No. PCT/JP2019/028972 filed Jul. 24, 2019, which claims the priority from Japanese Patent Application No. 2018-152121 filed in the Japanese Patent Office on Aug. 10, 2018 and PCT/JP2019/019714 filed May 17, 2019, the entire contents of which are hereby incorporated by reference.

TECHNICAL FIELD

The technique disclosed in the present specification relates to an information processing apparatus, an information processing method, and a video sound output system that execute an output process of an acoustic signal in synchronization with a video signal.

BACKGROUND ART

In recent years, a television apparatus (or an amplifier apparatus or the like connected to the television apparatus) that uses a sound localization technique for virtually localizing a sound source of reproduction sound at a desirable position is proposed (see PTL 1). Basically, left and right speakers can be arranged on the television apparatus, and stereo signals of two left and right channels can be reproduced to realize the sound localization. The number of channels of the sound signals can be increased, and the speakers can be multiplexed to control the sound field at a higher resolution. For example, an acoustic signal processing apparatus that uses a plurality of speakers to output sound and thereby increase the sound quality of a predetermined listening area is proposed (see PTL 2).

Meanwhile, an organic EL (Electroluminescence) technique or the like is used, and the size of the screen is increasing. The large screen can not only display one piece of content, such as a TV program, but can also display a plurality of pieces of content in parallel. For example, PIP (Picture in Picture) for displaying a video on a sub screen in a main screen displaying a specific video in the screen, PAP (Picture and Picture) for displaying another video outside of a specific video in the display screen, and the like are known (see PTL 3). In addition, the video sources displayed in parallel are not limited to broadcast content, and the video sources can be various types of content, such as network content delivered through the Internet and reproduction content output from Blu-ray or other disk reproduction apparatuses. For example, a hybrid terminal that handles both the broadcast content and the network content is proposed (see PTL 4).

CITATION LIST

Patent Literature

[PTL 1]
JP 2011-259299A
[PTL 2]
JP 2013-102389A
[PTL 3]
Japanese Patent No. 3526056
[PTL 4]
JP 2013-31046A

SUMMARY

Technical Problem

An object of the technique disclosed in the present specification is to provide an information processing apparatus, an information processing method, and a video sound output system that execute an output process of an acoustic signal in synchronization with a video signal.

Solution to Problem

A first aspect of the technique disclosed in the present specification provides
an information processing apparatus including a control section that detects a position of a sound source appearing in a video displayed on a screen of a display unit and that uses one or more vibrators to vibrate the display unit and thereby control output of sound such that a sound image of sound in synchronization with the video is localized at the position where the sound source appears on the screen displaying the video.

In a case of displaying videos of two or more video sources on individual windows, the control section localizes a sound image of a sound source detected from the video of each video source at a position where the sound source appears in the corresponding window.

In addition, a second aspect of the technique disclosed in the present specification provides
an information processing method including:
a detection step of detecting a position of a sound source appearing in a video displayed on a screen of a display unit; and
a control step of using one or more vibrators to vibrate the display unit and thereby control output of sound such that a sound image of sound in synchronization with the video is localized at the position where the sound source appears on the screen displaying the video.

In addition, a third aspect of the technique disclosed in the present specification provides
a video sound output system including:
a display unit;
a sound output unit that uses one or more vibrators to vibrate the display unit and thereby output sound; and
a control section that detects a position of a sound source appearing in a video displayed on a screen of the display unit and that controls the sound output unit such that a sound image of sound in synchronization with the video is localized at the position where the sound source appears on the screen displaying the video.

The "system" mentioned here denotes a logical set of a plurality of apparatuses (or functional modules that realize specific functions), and whether or not the apparatuses or the functional modules are in a single housing does not particularly matter.

Advantageous Effect of Invention

According to the technique disclosed in the present specification, an information processing apparatus, an information processing method, and a video sound output system that execute an output process of an acoustic signal in synchronization with a video signal can be provided.

Note that the advantageous effects described in the present specification are illustrative only, and the advantageous effects of the present invention are not limited to these. In addition, the present invention may also attain additional advantageous effects other than the advantageous effect described above.

Other objects, features, and advantages of the technique disclosed in the present specification will become apparent from more detailed description based on the embodiment described later and the attached drawings.

DESCRIPTION OF EMBODIMENT

Hereinafter, an embodiment of the technique disclosed in the present specification will be described in detail with reference to the drawings.

Figure 1:
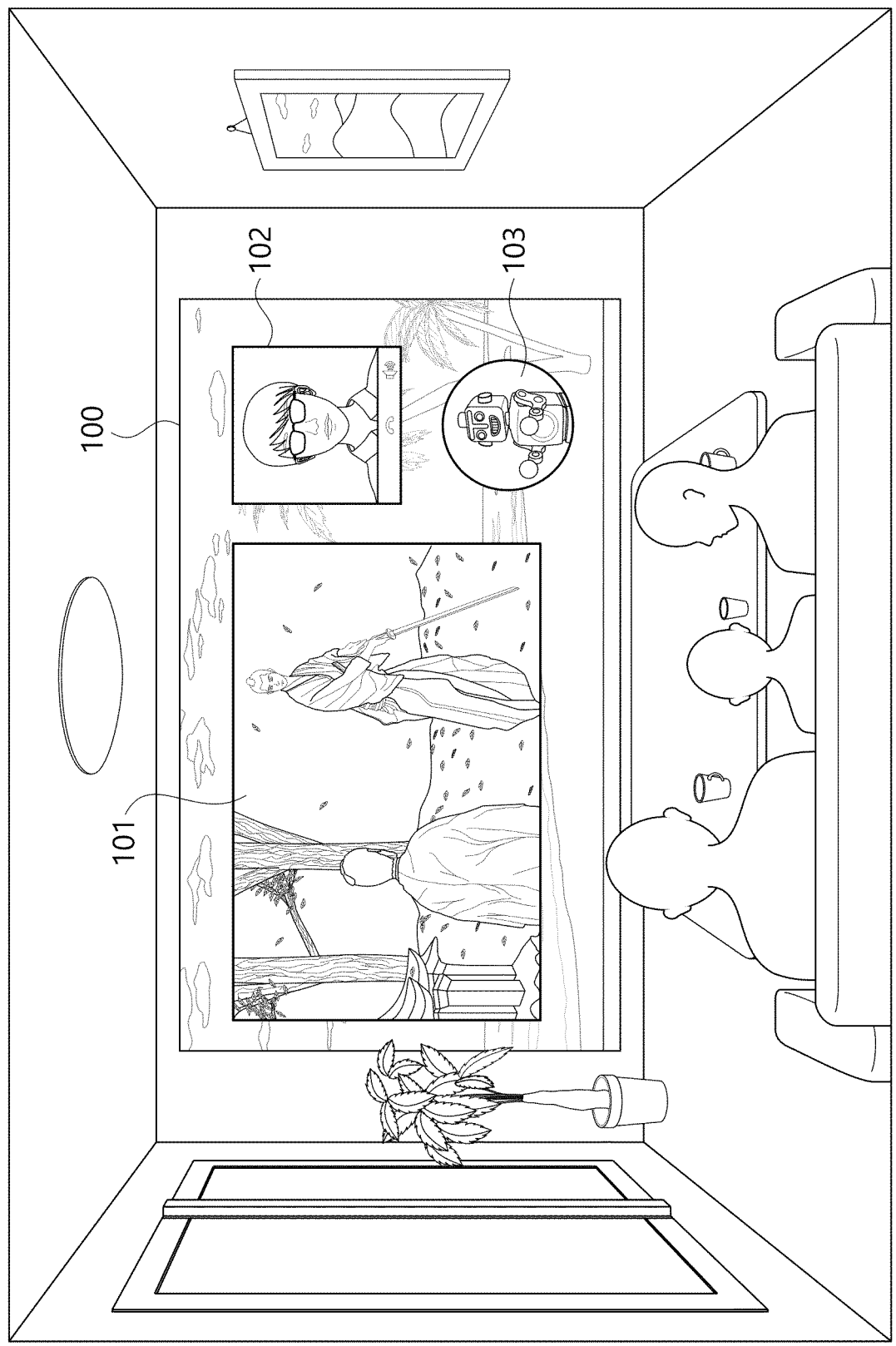
FIG. 1 is a diagram illustrating an example of an environment in which the technique disclosed in the present specification is applied.

FIG. 1 illustrates an example of an environment in which the technique disclosed in the present specification is applied. In FIG. 1, a television apparatus 100 is installed on a wall surface facing a plurality of users (such as family members) relaxing and sitting on a sofa of a living room. The television apparatus 100 includes a large screen using an organic EL technique or the like.

The television apparatus 100 is equipped with a speaker array including a plurality of speakers not illustrated or is externally connected. The speaker array may be configured to use one or more vibrators (actuators) two-dimensionally arrayed on the back side of the screen of the television apparatus 100 to vibrate the screen and thereby output sound. In addition, the arrangement position of the vibrators (actuators) is not limited to the back side of the screen, and the array is not limited to the two-dimensional array. It is assumed in the present embodiment that the television apparatus 100 can use the speaker array to control the sound field at a high resolution.

The television apparatus 100 can select and receive a broadcast signal through a built-in tuner or an external tuner. In addition, the television apparatus 100 is equipped with a network interface card and is capable of transmitting and receiving data related to visual communication, such as an OTT (Over the Top) service and a video conference provided by a provider. In addition, an application installed in advance, such as a sound agent and an assistant, can be executed on the television apparatus 100.

Therefore, at least one of plural pieces of content, such as on-air or recorded broadcast content, streaming content delivered by an OTT service, a video conference (or a Web conference) or other visual communication, and a character of a sound agent or an assistant, is displayed on the large screen of the television apparatus 100. In addition, a technique, such as PIP and PAP, can also be used to display two or more pieces of content in parallel at the same time on the large screen. In the example illustrated in FIG. 1, on-air broadcast content 101, visual communication 102, and a character 103 of a sound agent are displayed in parallel at the same time on the large screen of the television 100. In addition, although not illustrated in FIG. 1, graphics information, such as OSD (On Screen Display) generated in the television apparatus 100, can also be displayed on the large screen.

Note that, although the TV screens are installed on only one wall in the living room in the example illustrated in FIG. 1, the TV screens may be installed on the walls of two or more surfaces. Further, in a case where the TV screens are installed in succession on adjacent walls, a display method can be carried out, in which all of the TV screens are synchronously driven and, for example, the character of the sound agent or the like is continuously moved across the TV screens on two or more surfaces.

Figure 2:
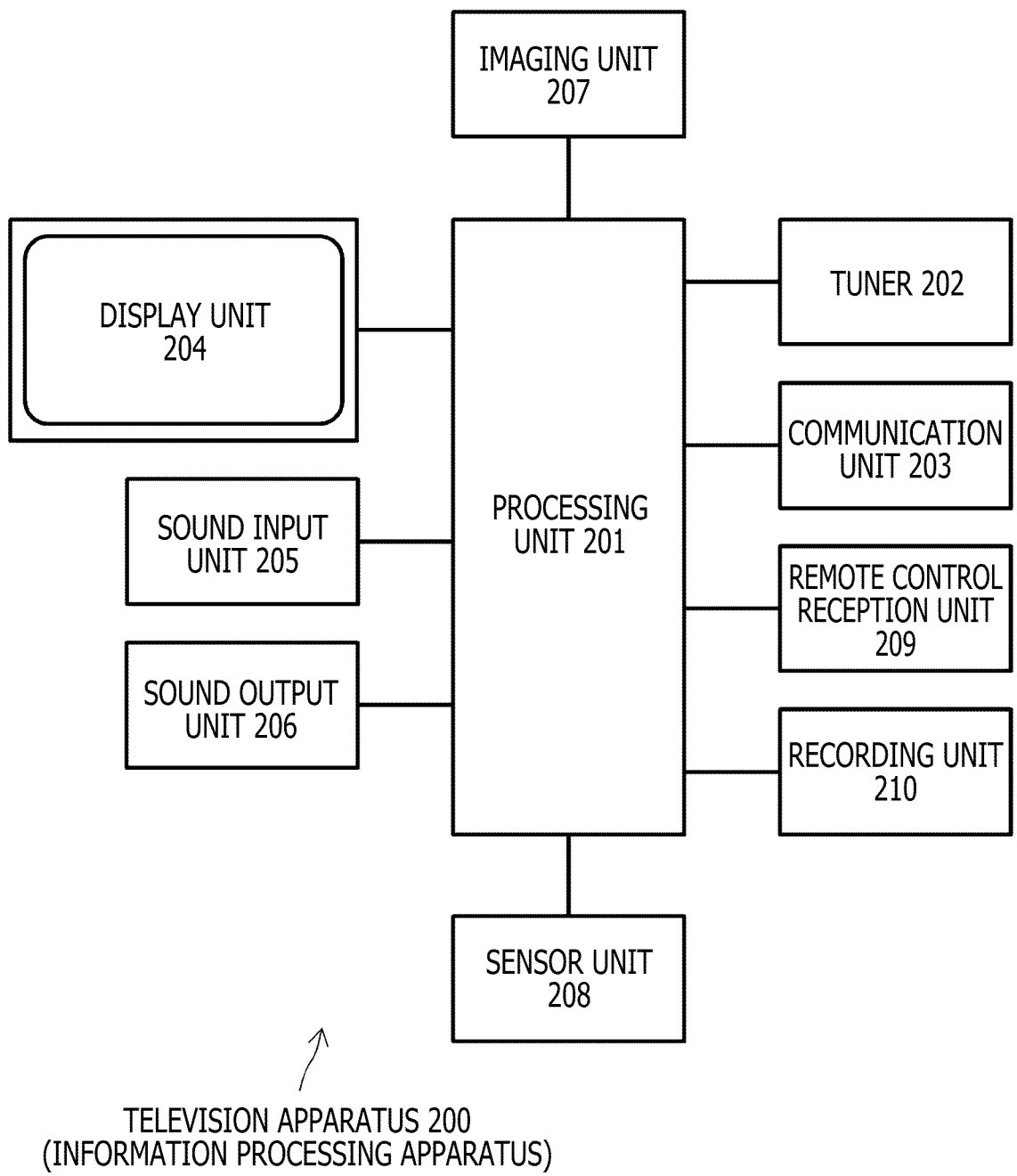
FIG. 2 is a diagram schematically illustrating an internal configuration example of a television apparatus 200.

FIG. 2 schematically illustrates an internal configuration example of a television apparatus 200. Here, the television apparatus 200 may be an information processing apparatus including a broadcast tuner. The illustrated television apparatus 200 includes a processing unit 201, a tuner 202, a communication unit 203, a display unit 204, a sound input unit 205, a sound output unit 206, an imaging unit 207, a sensor unit 208, a remote control reception unit 209, and a recording unit 210.

The tuner 202 selects and receives broadcast signals of terrestrial broadcasting and satellite broadcasting. In addition, the communication unit 203 uses wired communication, such as Ethernet (registered trademark), or wireless communication, such as Wi-Fi (registered trademark), to connect to an external network, such as the Internet. For example, the communication unit 203 transmits and receives data related to an OTT service or visual communication provided by the provider. In addition, the communication unit 203 includes a communication interface that transmits digital signals of video and sound of HDMI (registered trademark) (High Definition Multimedia Interface) or the like and can be used to externally connect a recording and reproducing device, such as Blu-ray and a hard disk, a game machine, and the like to the television apparatus 200. In addition, the communication unit 203 may be mutually connected to each CE device in a household through a home network according to a standard, such as DLNA (registered trademark) (Digital Living Network Alliance), for example, or may further have an interface function for an IoT (Internet of Things) device.

The display unit 204 includes, for example, an organic EL element and includes a large screen with an aspect ratio of 16:9. The display unit 204 is used to display a video, an EPG (Electronic Program Guide), and data broadcast content of program content selected and received by the tuner 202, display streaming content delivered by an OTT service, or display a video of visual communication such as a video conference. In addition, graphics, such as an image of a sound agent or other applications installed in advance on the television apparatus 200 and OSD generated in the television apparatus 200, are also displayed on the display unit 204. Note that a touch sensor may be superimposed on part or all of the area of the screen of the display unit 204.

The sound input unit 205 includes a sound collection element, such as a microphone, and is used to input sound generated in a room (in the living room illustrated in FIG. 1) in which the television apparatus 200 is installed. An example of the sound generated in the room includes a speech of a viewer of a TV program or a user using the sound agent. The sound input unit 205 may include a microphone array including a combination of plural microphones. In addition, part or all of the microphones may be externally connected to the television apparatus 200. Alternatively, a microphone mounted on a remote control for the television apparatus 200 may be included, or a microphone mounted on an external device of the television apparatus 200, such as a smartphone and a wearable device, may be included. In the case where the sound input unit 205 includes a plurality of microphones, a beamforming process can be executed to increase the sound collection sensitivity of the sound from a desirable sound source position, such as sound of the user talking to the sound agent, or conversely, to reduce the sound collection sensitivity of sound from an unnecessary sound source position, such as voice of other users and sound output from other AV devices in the room.

The sound output unit 206 is used for output of sound of program content or data broadcast content selected and received by the tuner 202, output of synthetic sound of sound agent function, and the like. The sound output unit 206 includes a sound generation element, such as a speaker. In the present embodiment, it is assumed that the sound output unit 206 includes a speaker array (multi-channel speaker or super multi-channel speaker) including a combination of plural speakers (part or all of the speakers may be externally connected to the television apparatus 200). Therefore, the sound output unit 206 can generate a sound field based on the output control of each speaker to localize the sound image at a desirable position or to make it difficult to hear the sound from a place other than the desirable position.

Other than cone type speakers, flat-panel speakers can be arranged in an array and used as the sound output unit 206. Obviously, a speaker array including a combination of different types of speakers can also be used as the sound output unit 206. In addition, the speaker array may also include one or more vibrators (actuators) that generate vibration to cause the display unit 204 to vibrate and thereby output sound. The vibrators (actuators) may be actuators added on to the display unit 204.

Figure 11:
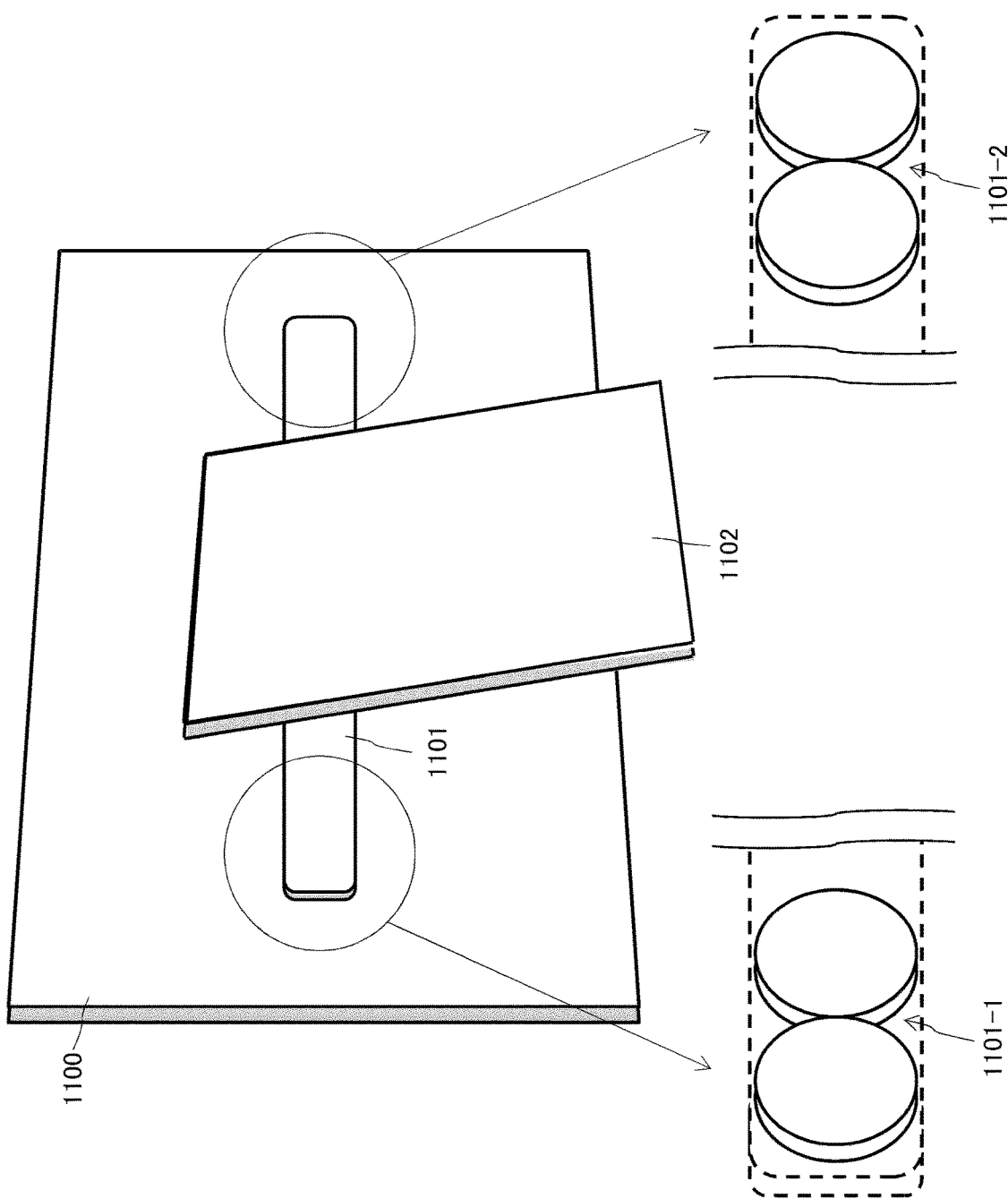
FIG. 11 is a diagram illustrating an application example of a screen vibration speaker technique.

FIG. 11 illustrates an example of applying the screen vibration speaker technique to a display. A display 1100 is supported by a stand 1102 on a rear surface. In addition, a speaker unit 1101 is attached to the back surface of the display 1100. A vibrator (actuator) 1101-1 is arranged on the left end of the speaker unit 1101, and a vibrator (actuator) 1101-2 is arranged on the right end to provide a speaker array. The vibrators (actuators) 1101-1 and 1101-2 can vibrate the display 1101 to output sound based on left and right sound signals, respectively. In addition, the stand 1102 may include a subwoofer that outputs low-frequency sound. Note that the display 1100 corresponds to the display unit 204 using an organic EL element.

The internal configuration of the television apparatus 200 will continuously be described with reference again to FIG. 2. The imaging unit 207 includes, for example, a camera including an image sensor, such as a CMOS (Complementary Metal Oxide Semiconductor) and a CCD (Charge Coupled Device), and mainly images, for example, a user in front of the large screen of the display unit 204 or a scene in the room in the front direction of the television apparatus 200. The imaging unit 207 may be, for example, a stereo camera using two cameras or a multi-camera using three or more cameras. In addition, part or all of the cameras may be externally connected to the television apparatus 200.

The sensor unit 208 mainly senses environment information in the room provided with the television apparatus 200. The configuration of the sensor unit 208, that is, what kind of sensor element is included, is optional. For example, the sensor unit 208 may include an object detection sensor or a depth sensor. The furniture installed in the room or the layout of the room can be detected based on a detection result of the object detection sensor or the depth sensor (if necessary, in conjunction with an image recognition result of an image captured by the imaging unit 207). In addition, the sensor unit 208 may also include an environment sensor, such as an illuminance sensor, a temperature sensor, and a humidity sensor, that detects environment information. In addition, the sensor unit 208 may also include an infrared sensor or a motion sensor to detect the position or the movement of the user in the room. In addition, the sensor unit 208 may also include a biosensor that detects the pulse, sweating, brain waves, myogenic potential, exhalation, and the like of the user. Part or all of the sensor units included in the sensor unit 208 may be externally or wirelessly connected to the television apparatus 200.

The remote control reception unit 209 executes a reception process of a remote control command transmitted from a remote control (not illustrated) by using infrared communication, near field communication, or the like. The operator of the remote control is, for example, the user viewing the television apparatus 200 in the living room illustrated in FIG. 1.

The recording unit 210 includes, for example, a large-capacity recording apparatus, such as an HDD (Hard Disc Drive), and is mainly used to record the program content received by the tuner 202. The recording unit 210 is installed in the television apparatus 200 in one case, and in another case, the recording unit 210 is externally connected to the television apparatus 200 through an interface, such as HDMI (registered trademark) (High Definition Multimedia Interface) and USB (Universal Serial Bus).

The processing unit 201 includes a processor and a memory and executes programs loaded on the memory to carry out various processes and comprehensively control the action in the television apparatus 200. In the processing unit 201, various applications are basically executed under an execution environment provided by an operating system (OS). For example, in a case where a multiprocessor can be used or in a case where the OS is capable of multithreaded execution, every unit of processing that can be executed in parallel can be read out to the memory and executed in parallel.

Examples of the process executed by the processing unit 201 include operations in the device 100, such as channel selection, volume adjustment, recording, and image quality adjustment, corresponding to remote control commands received by the remote control reception unit 209, an output process of video and sound of program content selected and received by the tuner 202, a reproduction output process of program content recorded in the recording unit 210, a reproduction output process of streaming content delivered by OTT service, execution of an application, control of the display of OSD, and the like. In addition, examples of the application executed by the processing unit 201 include a data broadcast application received through the tuner 202 or the communication unit 203, an application of OTT service, and an application, such as a sound agent and visual communication, installed in advance on the processing unit 201. In addition, the processing unit 201 can also execute plural agent applications in parallel, and the television apparatus 200 can function as a plurality of agent devices.

The television apparatus 200 performs hybrid video display in parallel, such as output of video and sound of the selected and received broadcast content, reproduction and output of the streaming content delivered by OTT service, reproduction and output of visual communication, such as a video conference, and display of graphics of the sound agent or the like. Therefore, the processing unit 201 includes a video memory including a plurality of planes for broadcast content, streaming content, visual communication, and graphics. In addition, when a plurality of pieces of video content is displayed at the same time, a multi-window is applied as also illustrated in FIG. 1. That is, in the processing unit 201, the resolution of each video of broadcast content, streaming content, visual communication, and graphics is converted according to the window size set for each video, and the video is copied to a window position on each plane. Subsequently, the planes in the video memory are superimposed in a predetermined order to generate one image frame. The image frame is temporarily stored in a video buffer, and then the display unit 204 displays the video.

In addition, the television apparatus 200 according to the present embodiment is characterized in that sound localization for bringing a sound image into line with an image is executed in sound signal processing.

If the sound corresponding to the video is localized at a position different from the display position of the video, the user viewing the screen feels uncomfortable. For example, when a plurality of performers appears in the window of broadcast content, and one or a plurality of video conference participants is on the window of visual communication, if the sound image of the voice spoken by the video conference participant is not localized in the window of visual communication, the user may be confused whose voice it is, or mutual understanding may be obstructed.

When all of the large screen is used to display a TV program in which a plurality of performers appears, if the voice spoken by a performer is localized at a place separated from the position where the performer is displayed, it is difficult for the user to identify the speaker, and the user feels uncomfortable. In addition, it is unnatural to continuously localize, at a certain place, the sound image of the sound agent moving in the screen. The problem of mismatch of the sound image and the image becomes more prominent with an increase in the size of the screen.

Further, as described above, if the sound image and the image do not match in the case where plural videos, such as video content of broadcast or streaming, visual communication, and sound agent, are displayed in parallel, the user may misunderstand the window generating the sound.

Therefore, the television apparatus 200 according to the present embodiment is configured to carry out a process of detecting the sound source appearing in the video, calculating the display position of the sound source on the screen, and localizing the sound generated from the sound source at the display position of the sound source to thereby bring the sound image into line with the image.

Hereinafter, processes executed by the television apparatus 200 to bring the sound images into line with images in displaying the video content (including broadcasting and OTT service), the visual communication, and the graphics will be described.

(1) Case of Video Content

In the case where the video is broadcast content, the sound source appearing in the video is a performer of the TV program (or a speaker displayed on the screen). For example, the face position of the performer in the image can be detected through video analysis to thereby detect the sound source. When a plurality of performers appears at the same time, the face position of each performer is detected as a sound source. Alternatively, the data of the face position of each performer may be transmitted as meta information of the broadcast content. When the TV program is displayed on the entire screen, the detected face position is the display position of the sound source. Further, in the case where the multi-window is applied, the face position in the window displaying the TV program is calculated as the display position of the sound source. Further, every time each performer speaks, sound signal processing is executed to localize the sound image of the sound at the position where the face of the performer is displayed on the screen, and the sound is output from the sound output unit 206.

Note that the process of bringing the sound image into line with the image in the streaming content delivered by the OTT service is similar to the process described above.

Figure 3:
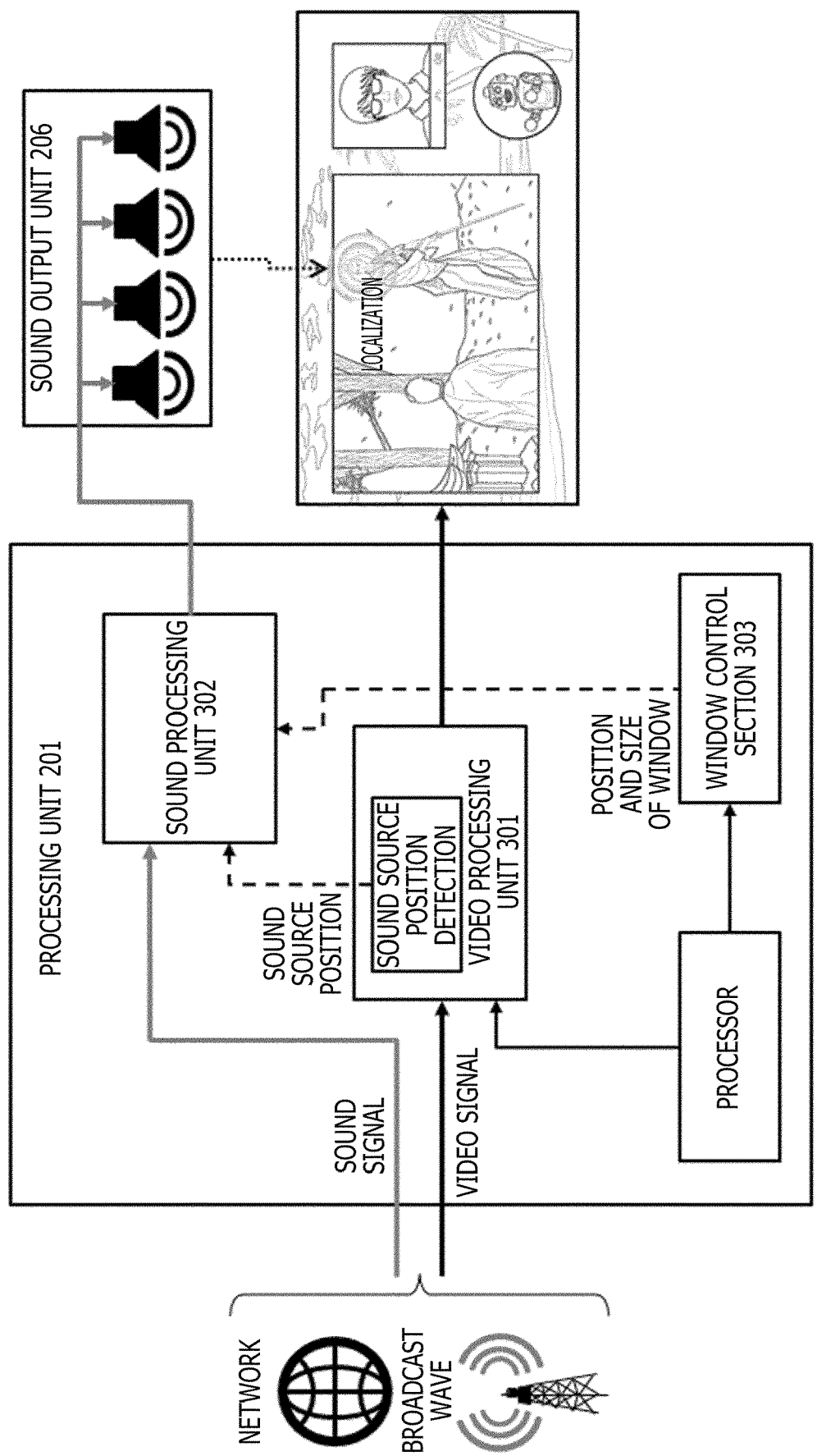
FIG. 3 is a diagram schematically illustrating a functional configuration for executing a process of bringing a sound image into line with an image in video transmission content.

FIG. 3 schematically illustrates a functional configuration for executing the process of bringing the sound image into line with the image in the video content. It is assumed here that each functional module illustrated in FIG. 3 is basically implemented in the processing unit 201.

The broadcast signal selected and received by the tuner 202 (not illustrated in FIG. 3) is demodulated and demultiplexed into video and sound. Subsequently, a decoding process is further applied to each of the video signal and the sound signal. FIG. 3 is based on the assumption that the video signal and the sound signal subjected to the decoding process are input.

In the case of the OTT service, the communication signal received by the communication unit 203 (not illustrated in FIG. 3) is demodulated and demultiplexed into video and sound. Subsequently a decoding process is further applied to each of the video signal and the sound signal. The transfer system of streams and the format of data may vary in each provider that provides the service. In any case, FIG. 3 is based on the assumption that the video signal and the sound signal subjected to the decoding process are input. Further, in a case where digital signals of video and sound are input from a recording and reproducing device, such as Blu-ray and a hard disk, a game machine, or the like through a digital communication interface, such as HDMI (registered trademark), it is assumed that the process according to the OTT service is carried out.

Once the video signal subjected to decoding is input, a video processing unit 301 detects the position of the sound source included in the video frame. The sound source is a speaker, such as a performer of the program. In a case where objects that output sound, such as musical instruments, are included in the frame, the positions of the objects as sound sources are also detected. The video processing unit 301 performs video analysis or the like in the course of, for example, the image quality adjustment process of the video signal to detect the face position of the speaker in the image and detect the sound source. Alternatively, in the case where the information of the sound source position is included in the meta information transmitted in association with the stream, the sound source position may be detected through the decoding process of the meta information. In the case where a plurality of speakers is included at the same time in the video, the video processing unit 301 detects each speaker as a sound source and detects the sound source position. The video signal processed by the video processing unit 301 is once written in a video plane in the video memory (not illustrated in FIG. 3), and then the video signal is superimposed with the image information of other planes and displayed and output to the screen of the display unit 204.

Once the sound signal subjected to decoding is input, a sound processing unit 302 uses a plurality of speakers included in the sound output unit 206 to output the sound. In a case where position information of the sound source is provided from the video processing unit 301, the sound processing unit 302 localizes the sound image at the position of the sound source, and the sound is output from the sound output unit 206.

In the case where the video frame is displayed on the entire screen of the display unit 204, the sound processing unit 302 converts the sound source position detected by the video processing unit 301 into information of the display position on the screen and localizes the sound image. On the other hand, in the case where the multi-window is applied to the screen of the display unit 204, once the sound processing unit 302 acquires, from a window control section 303, information of the display position and the size of the window allocated to the display of the video, the sound processing unit 302 converts the sound source position in the frame detected by the video processing unit 301 into the position in the window and adds the display position (offset) of the window to the position to thereby obtain information of the position of the sound source on the screen and localize the sound image.

In the case of the video including a plurality of sound sources (for example, in a case where a plurality of speakers appears in the video at the same time), the video processing unit 301 detects the sound source position of each speaker. In addition, the sound processing unit 302 separates the input sound signal into sound of each sound source (for example, each speaker) and localizes each sound source at the corresponding sound source position to output the sound from the sound output unit 206.

Note that, in a case where the television apparatus 200 includes a multiple-tuner or in a case where viewing of a TV program and using of an OTT service are performed at the same time, the process is carried out in parallel for each piece of video content.

(2) Case of Visual Communication

In the case where the video is visual communication, such as a video conference, the sound source appearing in the video is a participant of the video conference. For example, the face position of the attendance of the conference in the image can be detected through video analysis to detect the sound source. In a case where there is a plurality of participants in the conference, the face position of each participant of the conference is detected as a sound source. Subsequently, the face position of the participant of the conference is calculated as a display position of the sound source in the window of the visual communication. Further, every time a participant of the conference speaks, sound signal processing is executed to localize the sound image of the sound at the face position of the participant of the conference, and the sound is output from the sound output unit 206.

Figure 4:
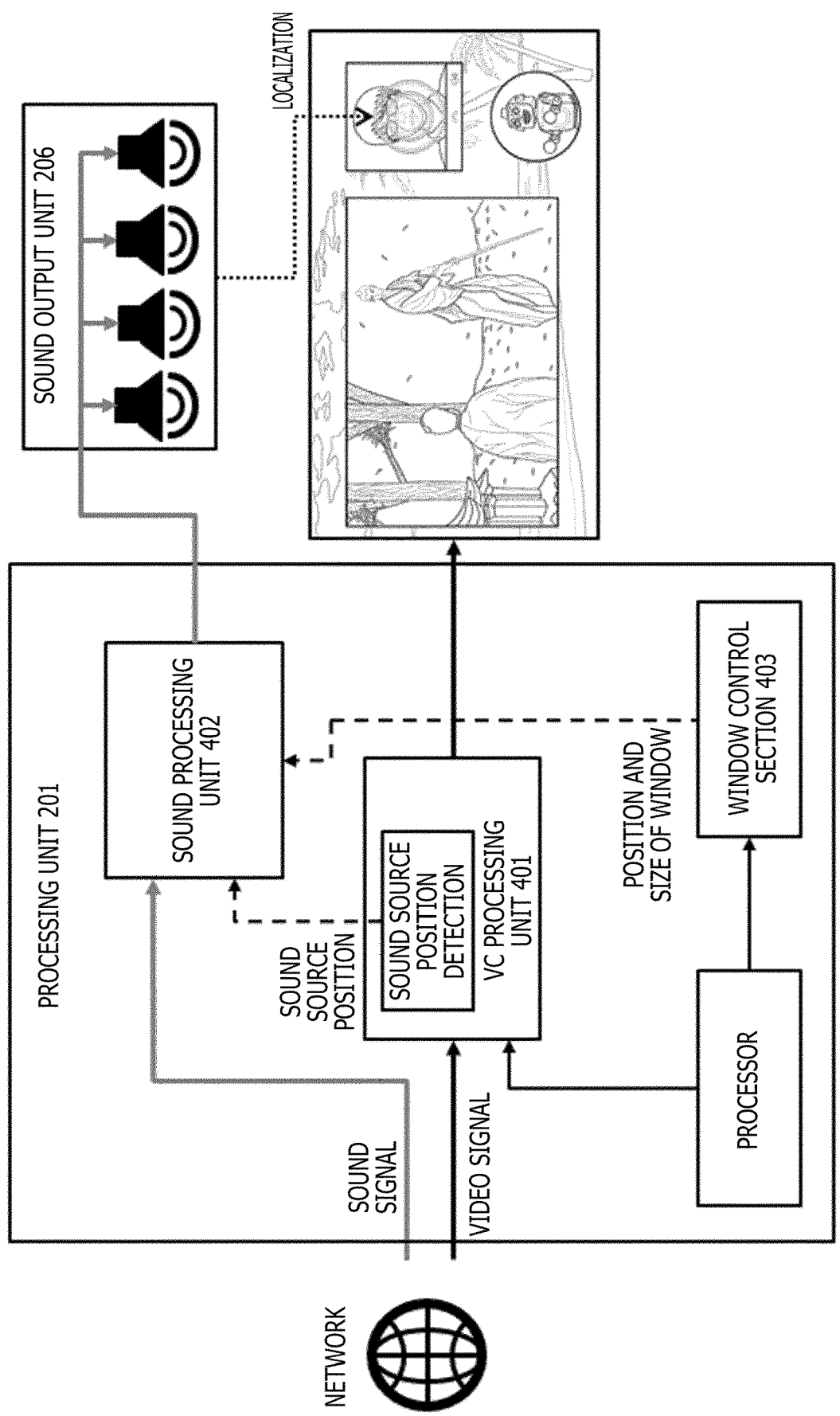
FIG. 4 is a diagram schematically illustrating a functional configuration for executing the process of bringing the sound image into line with the image in visual communication.

FIG. 4 schematically illustrates a functional configuration for executing a process of bringing the sound image into line with the image in the visual communication. Here, each functional module illustrated in FIG. 4 is basically implemented in the processing unit 201.

Once a communication signal for visual communication is received by the communication unit 203 (not illustrated in FIG. 4), the communication signal is demultiplexed into video and sound, and then the decoding process is further applied to each of the video signal and the sound signal. The transfer system of streams and the format of data may vary in each provider that provides the service. In any case, FIG. 4 is based on the assumption that the video signal and the sound signal subjected to the decoding process are input.

Once the video signal subjected to decoding is input, a visual communication (VC) processing unit 401 carries out a display process of the video of the video conference. Here, in a case where multi-point communication is used to perform the visual communication, the visual communication processing unit 401 executes a process of dividing the screen (or window area allocated to visual communication) of the display unit 204 into plural areas to display and output, to the divided areas, the video conference video imaged at other points (that is, allocate the divided area to each point). In addition, when the total number of divided areas is smaller than the number of connected points, the visual communication processing unit 401 switches the screen of each divided area. For example, in a case where the video of the point where the speaker is to speak next or the video of the point where the initiative is newly taken is hidden, the visual communication processing unit 401 switches the currently displayed video of another point to the video. The video signal subjected to processing by the visual communication processing unit 401 is once written in a visual communication plane in the video memory (not illustrated in FIG. 4), and then the video signal is superimposed with the image information of other planes and displayed and output to the screen of the display unit 204.

The visual communication processing unit 401 detects the position of the sound source included in the video frame. The sound source is a speaker, such as a participant of the video conference in the video. The visual communication processing unit 401 executes, for example, a face detection process to detect the face position of the participant of the conference in the video frame to detect the sound source. Further, in the case where the multi-point communication is used to perform the visual communication as described above, the visual communication processing unit 401 detects, as the position of the sound source, the divided area displaying the video of the point where the speaker is currently speaking.

Once the sound signal subjected to decoding is input, the sound processing unit 402 uses the plurality of speakers included in the sound output unit 206 to output the sound. In the case where the position information of the sound source is provided from the visual communication processing unit 401, the sound processing unit 402 localizes the sound image at the position of the sound source and outputs the sound from the sound output unit 206. In the case where the multi-point communication (described above) is used to perform the visual communication, the sound processing unit 402 localizes the sound image in the divided area displaying the video of the point where the speaker is currently speaking.

In the case where the display unit 204 displays the video of the visual communication on the entire screen, the sound processing unit 402 converts the sound source position detected by the visual communication processing unit 401 into information of the display position on the screen and localizes the sound image. In the case where the multi-point communication is used to perform the visual communication, the sound image is localized in the divided area reproducing the video of the point where the speaker is currently speaking.

On the other hand, in the case where the multi-window is applied to the screen of the display unit 204, once the sound processing unit 402 acquires, from the window control section 303, the information of the display position and the size of the window allocated to the visual communication, the sound processing unit 402 converts the sound source position detected by the visual communication processing unit 401 into the position in the window and adds the display position (offset) of the window to the position to thereby obtain information of the display position of the sound source on the screen and localize the sound image. In the case where the multi-point communication is used to perform the visual communication, the sound image is localized in the divided area reproducing the video of the point where the speaker is currently speaking.

In a case where a plurality of visual communications has logged in at the same time through the television apparatus 200, the process described above is carried out in parallel for each visual communication.

(3) Case of Graphics

The sound source of the sound agent is the video of the sound agent. Therefore, the display position of the sound agent can be acquired from a graphics processing unit that generates the video of the sound agent, to detect the position of the sound source. Further, in a case where the sound agent follows the user and moves in the large screen when the user moves in the room, the position of the sound source is detected based on the position information of the user. Further, every time the sound agent speaks, sound signal processing is executed to localize the sound image of synthetic sound of the sound agent at the display position of the sound agent, and the sound is output from the sound output unit 206.

Figure 5:
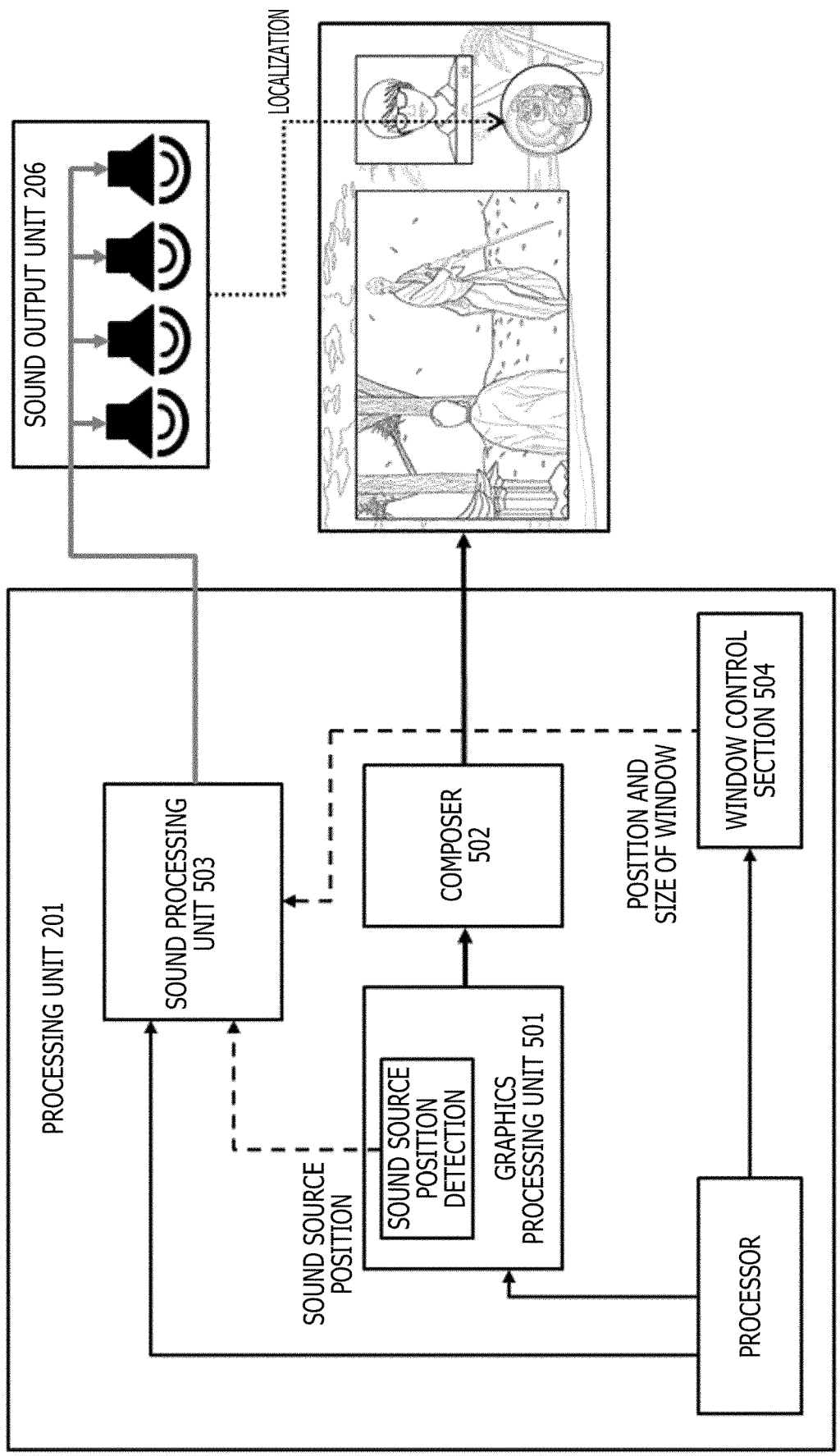
FIG. 5 is a diagram schematically illustrating a functional configuration for executing a process of bringing the sound image of a sound agent into line with the image.

FIG. 5 schematically illustrates a functional configuration for executing a process of bringing the sound image of the sound agent into line with the image. It is assumed here that each functional module illustrated in FIG. 5 is basically implemented in the processing unit 201.

In the present embodiment, it is assumed that an application for sound agent is installed in advance on the television apparatus 200. In the processing unit 201, such an application is executed to display the graphics (such as an animation character) of the sound agent on the screen of the display unit 204 or to output, from the sound output unit 206, the sound of a sound message from the sound agent. Here, there may be a case in which the application for sound agent is not executed in the television apparatus 200, and instead, the television apparatus 200 uses an external agent service. In this case, the television apparatus 200 uses the communication unit 203 to use interactive processing of the external agent service, and only the input and output of sound and the display of graphics of the sound agent are performed on the television apparatus 200.

A graphics processing unit 501 generates the graphics of the character of the sound source based on the result of the interactive processing executed by the processor in the processing unit 201 (or based on the interactive processing result received from the external agent service through the communication unit 203). Further, a composer 502 composes animation of the generated character. The image of the composed character animation is once written in a graphics plane in the video memory (not illustrated in FIG. 5), and then the image is superimposed with image information of other planes and displayed and output on the screen of the display unit 204.

Further, the graphics processing unit 501 outputs, to the sound signal processing unit 503, information regarding the position for displaying the graphics of the sound agent on the screen of the display unit 204.

A sound signal processing unit 503 synthesizes sound of a message (text) of the sound agent generated by the processor in the processing unit 201 (or external agent service) and uses the plurality of speakers included in the sound output unit 206, to output the sound. As described above, in the case where the information of the display position of the sound agent is provided from the graphics processing unit 501, the sound signal processing unit 503 localizes the sound image at the display position and outputs the sound of the sound agent from the sound output unit 206.

Figure 6:
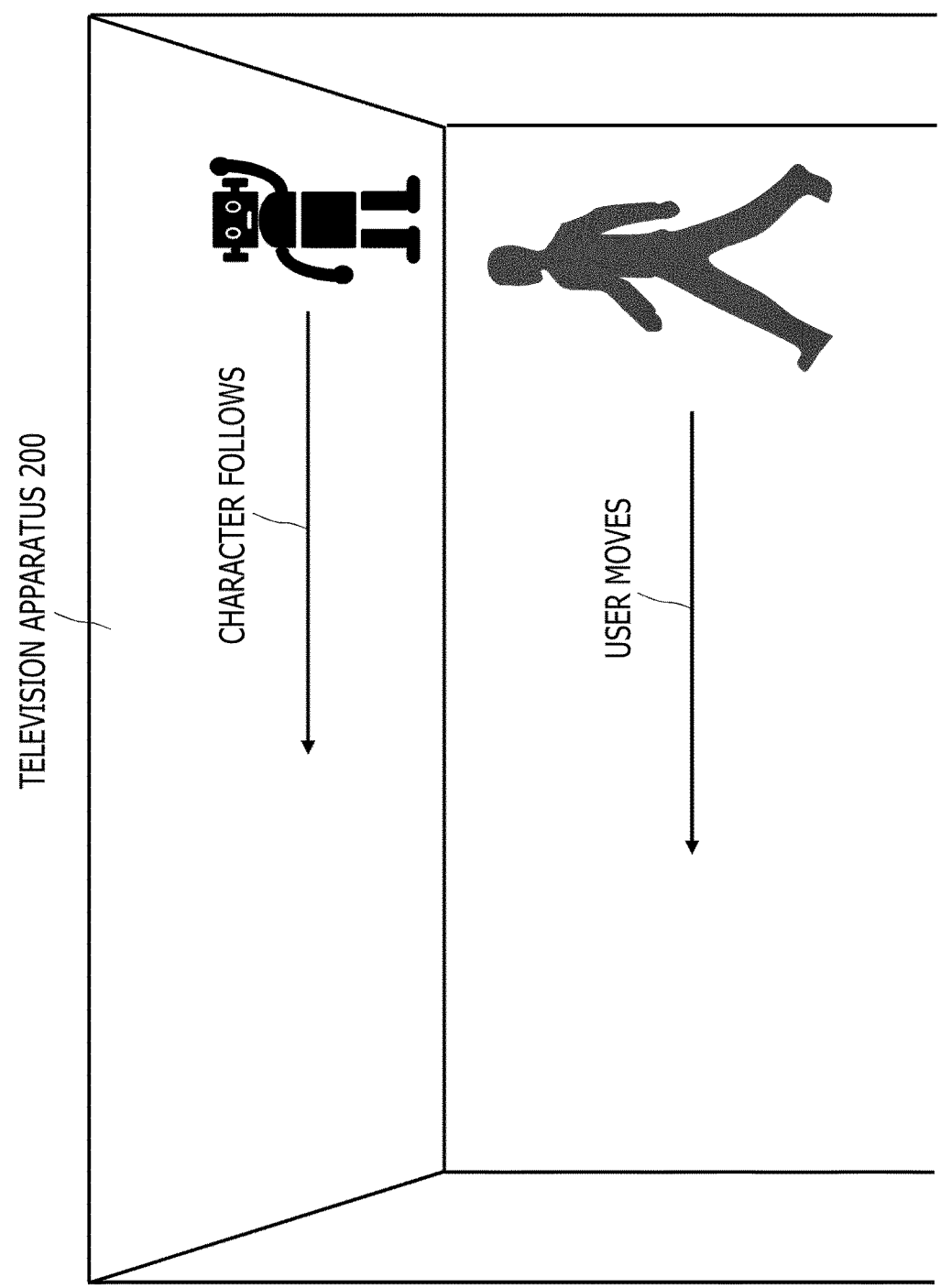
FIG. 6 is a diagram illustrating a state in which the sound agent moves in a large screen according to the movement of an interacting user.

In the present embodiment, it is assumed that the sound agent follows the user and moves in the large screen when the user interacting with the sound agent moves in the room as illustrated in FIG. 6. In addition, the captured image of the imaging unit 207 or the sensor unit 208 including an infrared sensor or a motion sensor can be used to detect the position of the user moving in the room.

Figure 7:
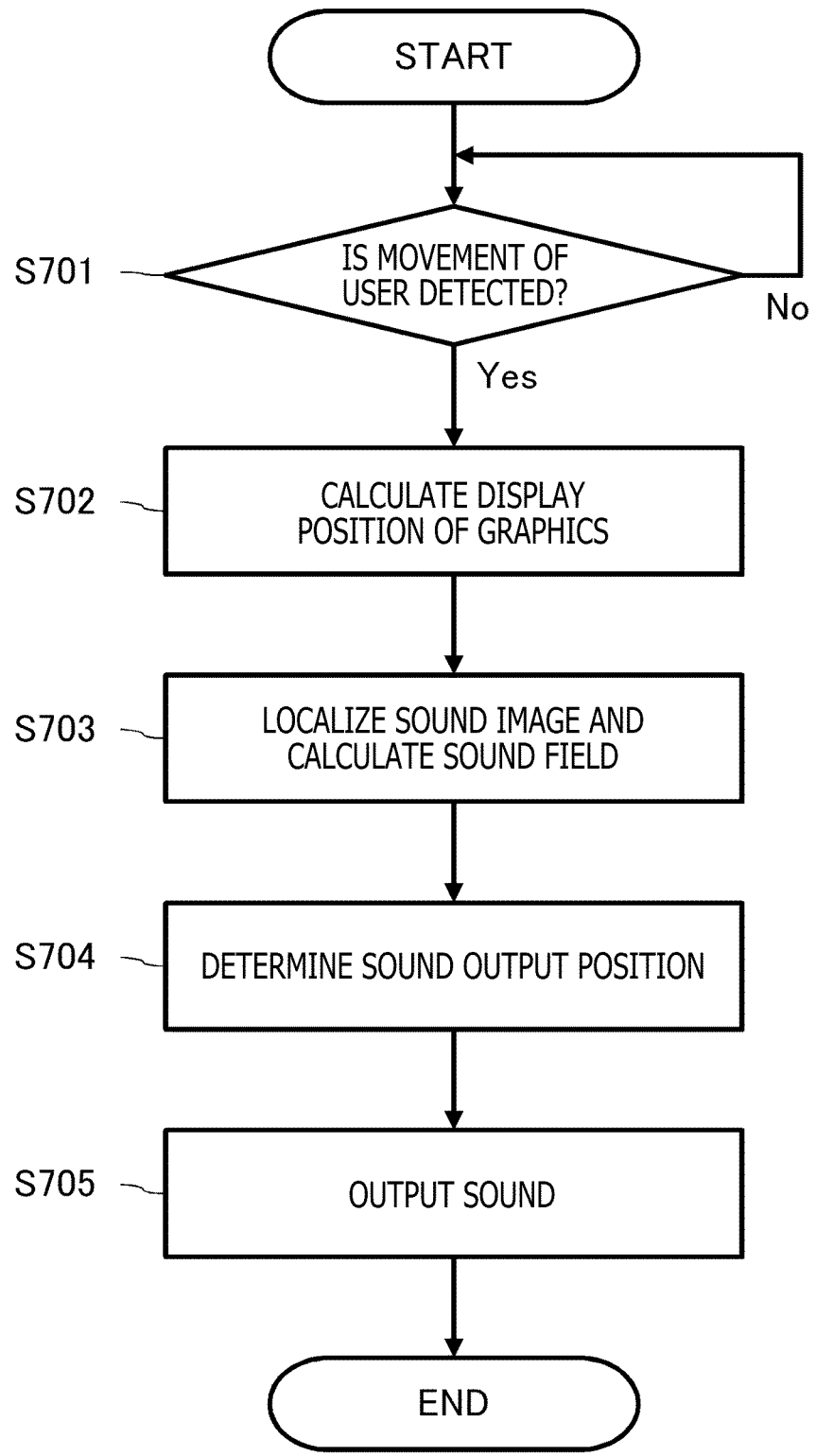
FIG. 7 is a flow chart illustrating a processing procedure for controlling sound output of the sound agent according to a position of the user.

FIG. 7 illustrates, in a form of a flow chart, a processing procedure for controlling the sound output of the sound agent according to the position of the user. It is assumed that the illustrated processing procedure is executed under the control of the processor in the processing unit 201.

When the captured image of the imaging unit 207 or the sensor unit 208 including an infrared sensor or a motion sensor is used to detect the position of the user moving in the room (or movement from the position detected last time) (Yes in step S701), the graphics processing unit 501 calculates the position for displaying the graphics of the sound agent on the screen of the display unit 204, based on the position of the user (step S702). In addition, the graphics processing unit 501 outputs, to the sound signal processing unit 503, the information regarding the position for displaying the graphics of the sound agent on the screen of the display unit 204.

Next, the sound signal processing unit 503 localizes the sound image of the sound of the sound agent and calculates the sound field, based on the information of the display position of the sound agent provided from the graphics processing unit 501 (step S703).

Further, the sound signal processing unit 503 determines the sound output positions for outputting the sound of the sound agent from among the plural speakers included in the sound output unit 206 in order to realize the sound field calculated in the preceding step S703 (step S704) and outputs the sound of the sound agent from the sound output positions (step S705).

Further, there is also a case of generating a sound effect according to the graphics display of OSD, UI (User Interface), or the like. The sound effect has a role of notifying the user of the generation of an event that the user needs to quickly respond. In such a case, the sound image of the sound effect is also localized at the display position of the graphics as in the case of the sound agent, and the sound effect more effectively echoes in the ears of the user.

When the processor in the processing unit 201 detects, during the execution of the application, an event for which graphics of ODS, UI, or the like need to be displayed, the processor instructs the graphics processing unit 501 to display the graphics.

The graphics processing unit 501 generates the graphics of OSD, UI, or the like based on the instruction from the processor in the processing unit 201. Further, the composer 502 composes the generated graphics. The image of the composed graphics is once written in the graphics plane in the video memory (not illustrated in FIG. 5), and then the image is superimposed with image information of other planes and displayed and output to the screen of the display unit 204. Further, the graphics processing unit 501 outputs, to the sound signal processing unit 503, information regarding the position for displaying the graphics of OSD, UI, or the like on the screen of the display unit 204.

The sound signal processing unit 503 synthesizes the sound effect for the graphics of OSD, UI, or the like and uses a plurality of speakers included in the sound output unit 206 to output the sound. As described above, in the case where the information of the display position of graphics is provided from the graphics processing unit 501, the sound signal processing unit 503 localizes the sound image at the display position and outputs the sound effect for the graphics from the sound output unit 206.

Figure 8:
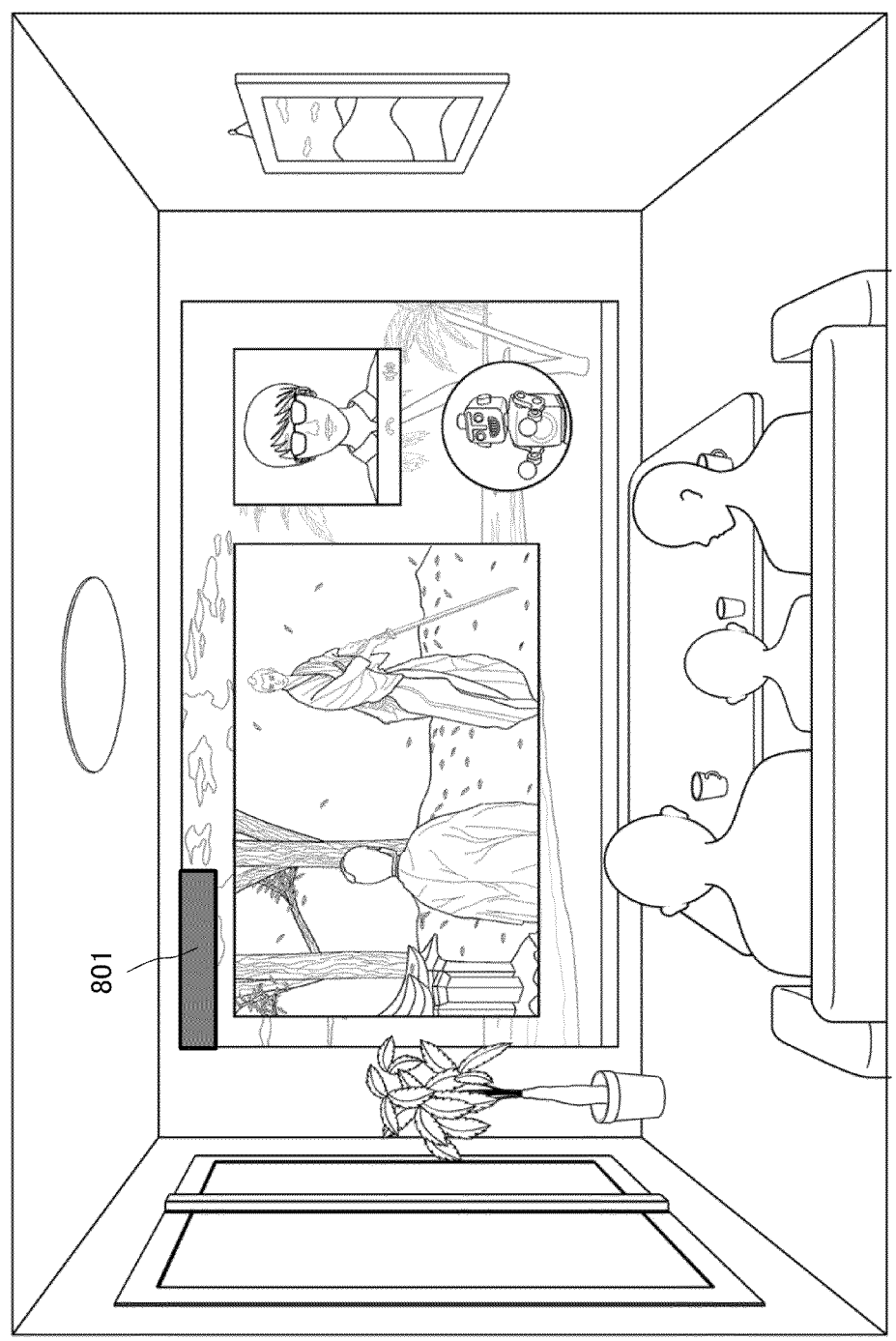
FIG. 8 is a diagram illustrating a state in which OSD appears from an upper left end of the screen.

FIG. 8 illustrates a state in which OSD indicated by reference number 801 appears from the upper left end of the screen. When a peripheral section of the large screen is used to display graphics, the user may not notice the graphics. In the case of the multi-window as illustrated in FIG. 1, the display of the screen is complicated in the first place, and the OSD is hidden in the texture of wall paper or the like so that it is difficult for the user to find the display place of the graphics. In addition, the generation of a sound effect, such as warning sound, in synchronization with the display of OSD does not provide a clue for the user to find the display when the sound effect is emitted from a place other than the display place of OSD. On the other hand, according to the present embodiment, the sound effect is emitted from the place of the appearance of OSD. Therefore, the user consequently looks in the direction of the sound image position, and the user can easily find the display of OSD.

The functional configurations for bringing the sound image into line with the image in the television apparatus 200 have been separately described above for the video content, the visual communication, and the graphics. In the present embodiment, the television apparatus 200 adopts the multi-window system to display the video content, the visual communication, and the graphics in parallel and to carry out the processes of brining the sound images into line with the images in parallel.

Figure 9:
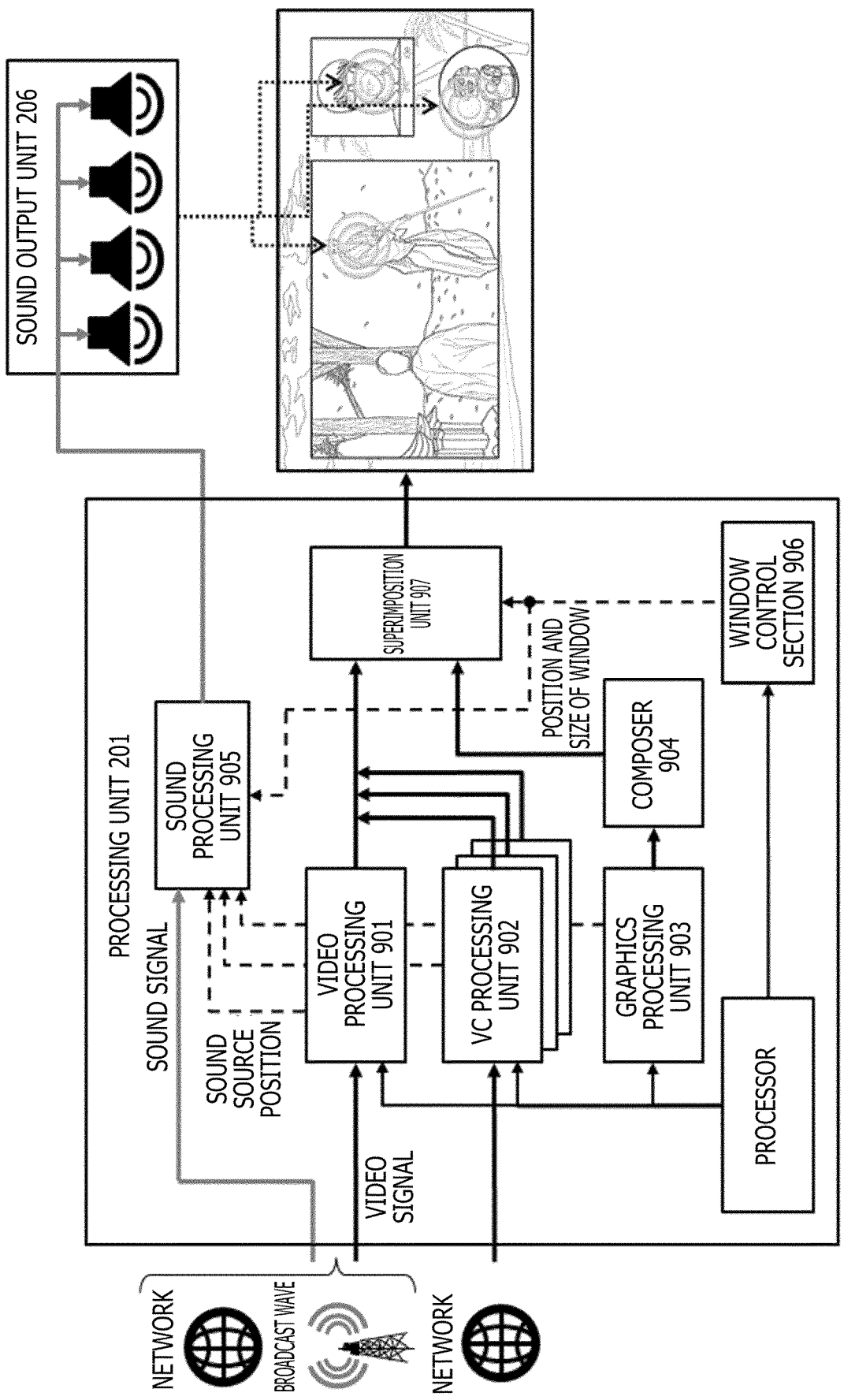
FIG. 9 is a diagram illustrating a configuration example of a processing unit 201 that carries out, in parallel, processes of bringing sound images into line with a plurality of images.

FIG. 9 illustrates a configuration example of the processing unit 201 that displays the video content, the visual communication, and the graphics in parallel and that carries out the processes of bringing the sound images into line with the images in parallel.

The signal provided by the broadcast service or the OTT service is demultiplexed into video and sound, and a decoding process is further applied to each of the video signal and the sound signal. Subsequently, the video signal and the sound signal are input to a video processing unit 901 and a sound processing unit 905, respectively.

Once the video signal subjected to decoding is input, the video processing unit 901 detects the position of the sound source included in the video frame. The sound source is a speaker, such as a performer of the program. In a case where objects that output sound, such as musical instruments, are included in the frame, the positions of the objects are also detected as sound sources. The video processing unit 901 performs video analysis or the like in the course of, for example, the image quality adjustment process of the video signal to detect the face position of the speaker in the image to detect the sound source. In the case where a plurality of speakers is included at the same time in the video, the video processing unit 901 detects each speaker as a sound source and detects the sound source position. The video signal processed by the video processing unit 901 is output to a superimposition unit 907 and is once written in the video plane in the video memory (not illustrated in FIG. 9).

Once the information of the display position and the size of the window allocated to the display of the video is acquired from a window control section 906, the sound processing unit 905 converts the sound source position in the frame detected by the video processing unit 301 into the position in the window and adds the display position (offset) of the window to the position to thereby obtain information of the position of the sound source on the screen and localize the sound image.

Once the video signal subjected to decoding is input, the visual communication processing unit 902 carries out the display process of the video of the video conference and also detects the position of the sound source included in the video frame. The sound source is a speaker, such as a participant of the video conference in the video. In the case where the multi-point communication (described above) is used to perform the visual communication, the visual communication processing unit 902 detects, as the position of the sound source, the divided area displaying the video of the point where the speaker is currently speaking. The video signal processed by the visual communication processing unit 902 is output to the superimposition unit 907 and is once written in the visual communication plane in the video memory (not illustrated in FIG. 9).

In the case where a plurality of visual communications has logged in at the same time through the television apparatus 200, the visual communication process is carried out in parallel for each visual communication.

Once the information of the display position and the size of the window allocated to the display of the visual communication is acquired from the window control section 906, the sound processing unit 905 converts the sound source position provided from the visual communication processing unit 902 into the position in the window and adds the display position (offset) of the window to the position to thereby obtain the information of the position of the sound source on the screen and localize the sound image. Further, in the case where the multi-point communication (described above) is used to perform the visual communication, the sound processing unit 905 localizes the sound image in the divided area displaying the video of the point where the speaker is currently speaking.

The graphics processing unit 903 generates the graphics of the character of the sound agent based on the result of interactive processing executed by the processor in the processing unit 201. Further, the composer 904 composes the animation of the generated character. The image of the composed character animation is once written in the graphics plane in the video memory (not illustrated in FIG. 9). Further, the graphics processing unit 903 outputs the information regarding the position for displaying the graphics of the sound agent on the screen of the display unit 204 to the sound signal processing unit 905.

The sound signal processing unit 905 synthesizes the sound of the message (text) of the sound agent generated by the processor in the processing unit 201. Further, the sound processing unit 905 localizes the sound image of the sound of the character at the display position of the graphics provided from the graphics processing unit 903 and outputs the sound from the sound output unit 206.

The superimposition unit 907 once writes the video signal output from the video processing unit 901 in the video plane in the video memory. At that time, the superimposition unit 907 acquires, from the window control section 906, the information of the display position and the size of the window allocated to the display of the video and writes the video in the window area allocated to the display of the video on the video plane.

Further, the superimposition unit 907 once writes the video signal output from the visual communication processing unit 902 in the visual communication plane in the video memory. At that time, the superimposition unit 907 acquires, from the window control section 906, the information of the display position and the size of the window allocated to the display of the visual communication and writes the video in the window area allocated to the display of the video on the visual communication plane.

Further, the superimposition unit 907 writes the video of the character and the graphics of OSD, UI, or the like output from the composer 904 in the graphics plane.

Figure 10:
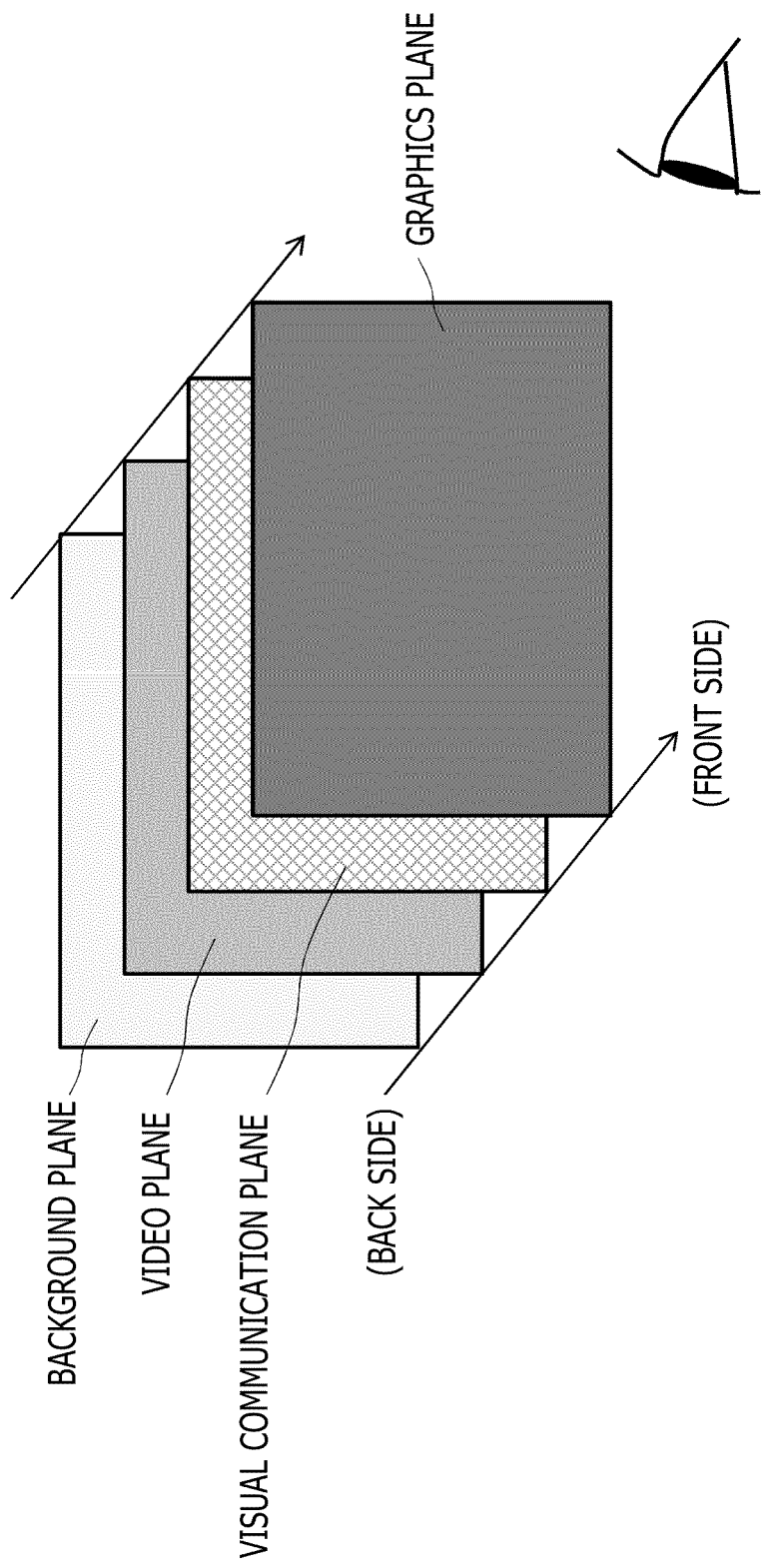
FIG. 10 is a diagram illustrating a state of superimposing planes in a video memory.

Further, the superimposition unit 907 superimposes plural planes in the video memory in a predetermined order to complete one image frame. In the present embodiment, the background plane, the video plane, and the graphics plane are sequentially superimposed from the back side toward the front as illustrated in FIG. 10. However, the order of arrangement of the planes is optional. The image frame is subsequently displayed and output to the screen of the display unit 204. The display of the plane on the front side is prioritized. In the screen configuration example of the television apparatus 100 illustrated in FIG. 1, the windows 101 and 102 of the video content, such as a TV program, and the visual communication and the character 103 of the sound agent are arranged not to overlap with each other, and in a case where at least part of the areas overlap with each other, the video on the back side is hidden by the video on the front side.

Example 1

The technique according to the present disclosure can be applied to various products. For example, the technique according to the present disclosure can be applied to an operating room system. A case of applying the technique according to the present disclosure to the operating room system will be described below.

Figure 12:
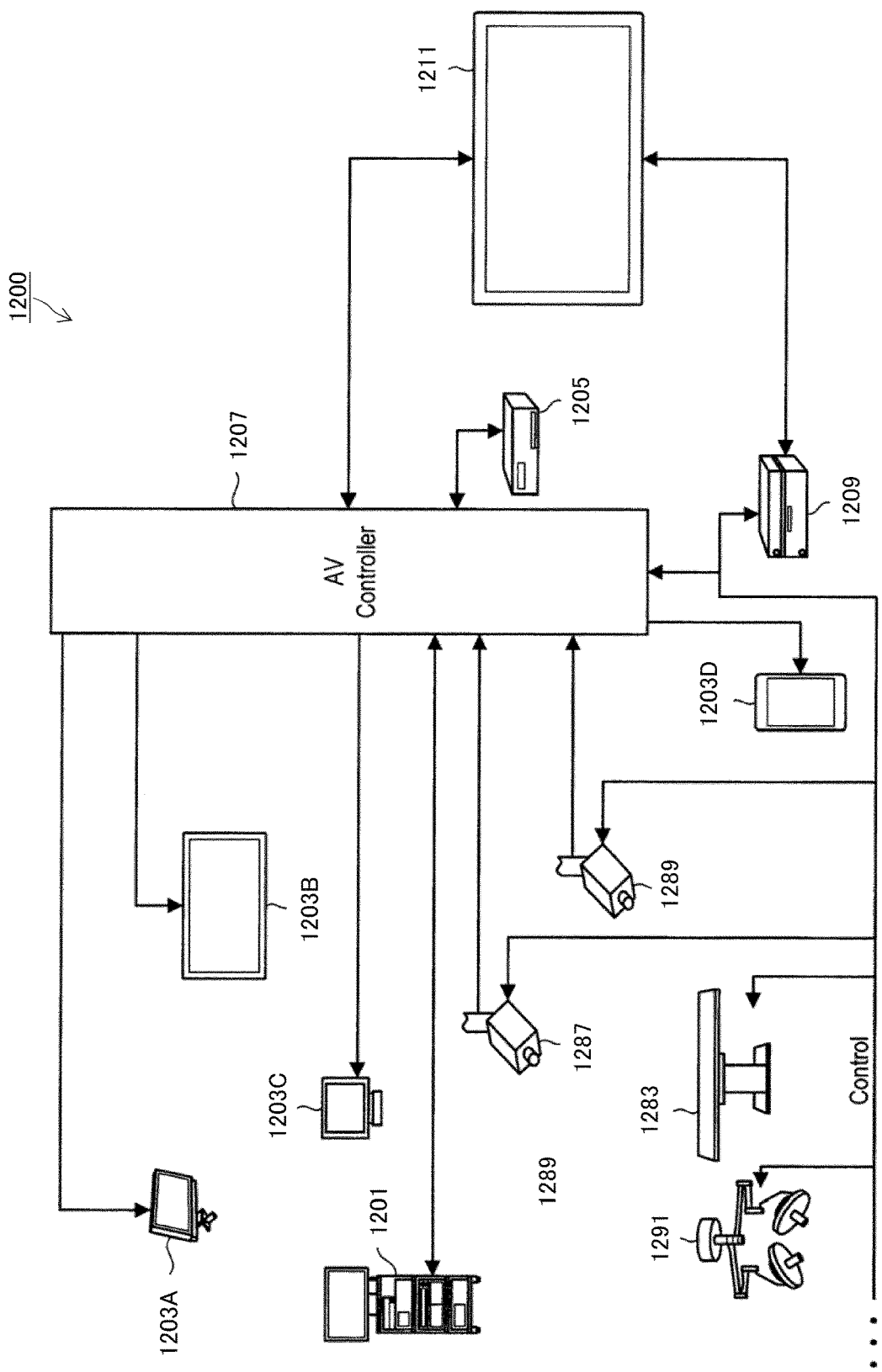
FIG. 12 is a diagram illustrating an overall configuration of an operating room system 1200.

FIG. 12 schematically illustrates an overall configuration of an operating room system 1200 in which the technique according to the present disclosure can be applied. The illustrated operating room system 1200 includes an audio-visual controller (AV Controller) 1207 and an operating room control apparatus 1209. The audio-visual controller 1207 and the operating room control apparatus 1209 are connected to each other and capable of cooperating with each other.

Various apparatuses may be installed in an operating room. In the example illustrated in FIG. 12, a group 1201 of various apparatuses for endoscopic surgery, a ceiling camera 1287 that is provided on the ceiling of the operating room and that images an area around the hands of an operator, an operating room camera 1289 that is provided on the ceiling of the operating room and that images the state of the entire operating room, a plurality of display apparatuses 1203A to 1203D, a recorder 1205, a patient bed 1283, a light 1291, and the like are installed in the operating room.

Among the apparatuses, the apparatus group 1201 belongs to an endoscopic surgery system and includes an endoscope, a display apparatus that displays an image captured by the endoscope, and the like. Each apparatus belonging to the endoscopic surgery system is also called a medical device. On the other hand, the display apparatuses 1203A to D, the recorder 1205, the patient bed 1283, and the light 1291 are apparatuses installed in the same operating room that do not belong to the endoscopic surgery system. Each apparatus not belonging to the endoscopic surgery system is also called a non-medical device. The audio-visual controller 1207 and the operating room control apparatus 1209 cooperate with each other to control the actions of the medical devices and the non-medical method devices.

The audio-visual controller 1207 comprehensively controls processes related to image display in the medical devices and the non-medical devices in the operating room system 1200. Here, among the apparatuses included in the operating room system 1200, the apparatus group 1201, the ceiling camera 1287, and the operating room camera 1289 are apparatuses (hereinafter, also referred to as "transmission source apparatuses") with functions for transmitting information (hereinafter, also referred to as "display information") to be displayed during surgery. In addition, the display apparatuses 1203A to 1203D are apparatuses (hereinafter, also referred to as "output destination apparatuses") that output display information. In addition, the recorder 1205 is an apparatus serving as both a transmission source apparatus and an output destination apparatus. In the operating room system 1200, the audio-visual controller 1207 has a function for controlling the actions of the transmission source apparatuses and the output destination apparatuses, acquiring display information from the transmission source apparatuses, transmitting the display information to the output destination apparatuses, and causing the output destination apparatuses to display or record the display information. Note that the display information includes various images captured during surgery, various types of information regarding surgery (for example, physical information of patient, past examination result, and information regarding surgical method), and the like.

Specifically, information regarding an image of a surgery site in a body cavity of the patient imaged by the endoscope is transmitted as display information from the apparatus group 1201 to the audio-visual controller 1207. In addition, information regarding an image of the area around the hands of the operator imaged by the ceiling camera 1287 is transmitted as display information from the ceiling camera 1287 to the audio-visual controller 1207. In addition, information regarding an image indicating the state of the entire operating room imaged by the operating room camera 1289 is transmitted as display information from the operating room camera 1289 to the audio-visual controller 1207. Note that, in a case where another apparatus (not illustrated) with imaging function further exists in the operating room system 1200, the audio-visual controller 1207 may acquire, as display information, information regarding an image captured by the other apparatus from the other apparatus.

In addition, the audio-visual controller 1207 records, in the recorder 1205, information regarding an image captured in the past by an apparatus having the imaging function as described above. The audio-visual controller 1207 can acquire, as display information, the information regarding the image captured in the past from the recorder 1205. Note that various types of information regarding surgery may also be recorded in advance in the recorder 1205.

The audio-visual controller 1207 causes at least one of the display apparatuses 1203A to 1203D as output destination apparatuses to display the display information acquired from the transmission source apparatuses (that is, images captured during surgery and various types of information regarding surgery). In the example illustrated in FIG. 12, the display apparatus 1203A is a display apparatus installed and hung from the ceiling of the operating room. The display apparatus 1203B is a display apparatus installed on a wall surface of the operating room. The display apparatus 1203C is a display apparatus installed on a desk in the operating room. In addition, the display apparatus 1203D is, for example, a mobile device with display function, such as a tablet PC (Personal Computer).

In addition, although not illustrated in FIG. 12, the operating room system 1200 may further include an apparatus installed outside of the operating room. Examples of the apparatus installed outside of the operating room include a server connected to a network constructed inside and outside of the hospital, a PC used by medical staff, and a projector installed in a conference room of the hospital. Further, the operating room system 1200 may include an apparatus installed outside of the hospital for the purpose of telemedicine or the like. In such a case, the audio-visual controller 1207 can also display the display information on a display apparatus of another hospital through a video conference system or the like.

The operating room control apparatus 1209 comprehensively controls processes other than the image display in the non-medical devices. For example, the operating room control apparatus 1209 controls the drive of the patient bed 1283, the ceiling camera 1287, the operating room camera 1289, and the light 1291.

A centralized operation panel 1211 is provided on the operating room system 1200. The user (such as an operator) can provide an instruction regarding the image display to the audio-visual controller 1207 and provide an instruction regarding the action of the non-medical device to the operating room control apparatus 1209 through the centralized operation panel 1211. The centralized operation panel 1211 includes a touch panel provided on the display surface of a display apparatus.

Figure 13:
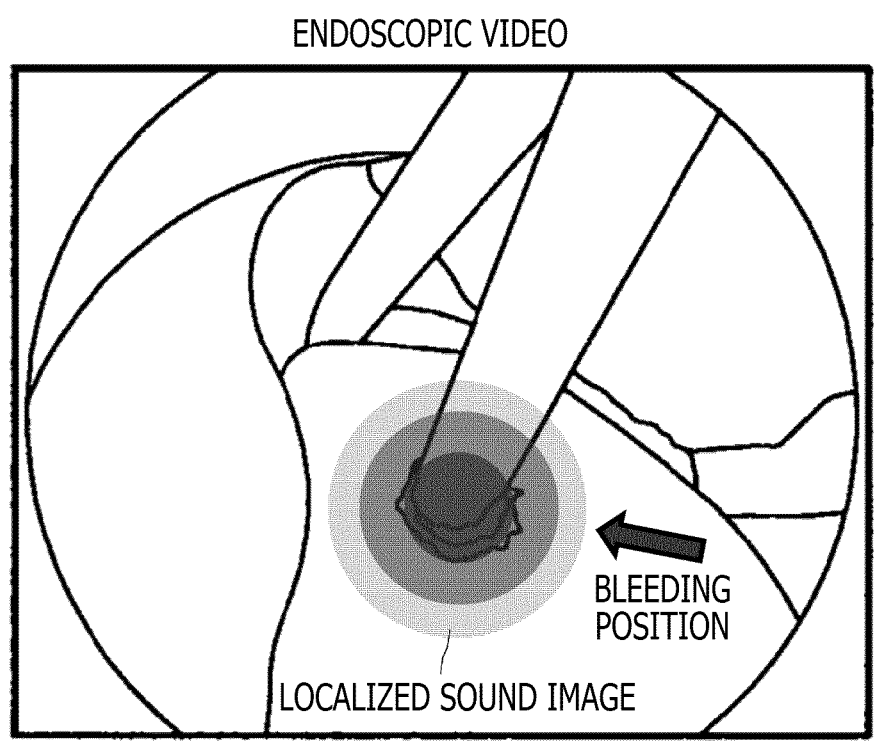
FIG. 13 is a diagram illustrating a state of localizing a sound image of warning sound on a screen of an endoscopic video displaying a surgery site.
Figure 14:
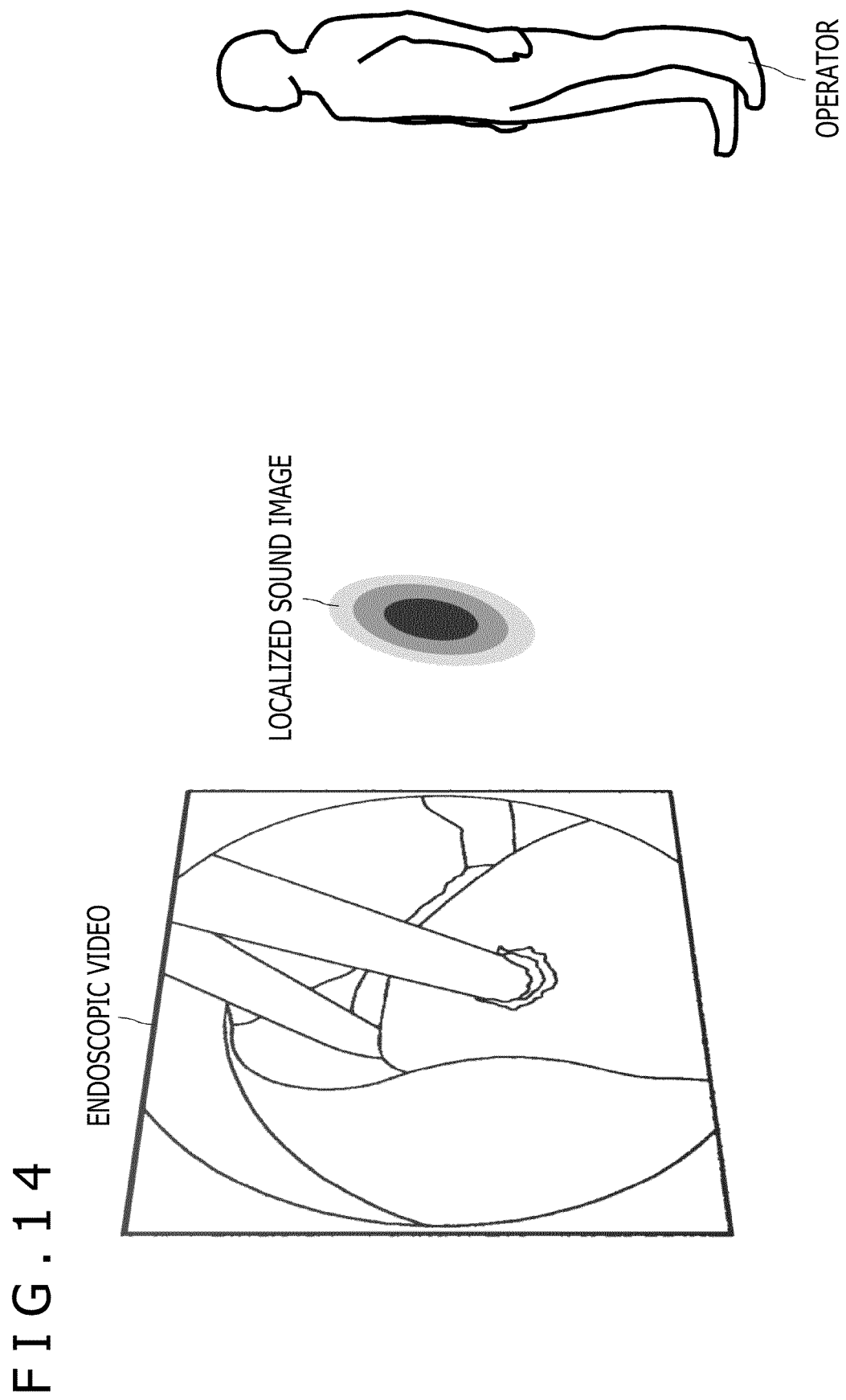
FIG. 14 is a diagram illustrating a state of localizing the sound image of the warning sound on the screen of the endoscopic video displaying the surgery site.
Figure 15:
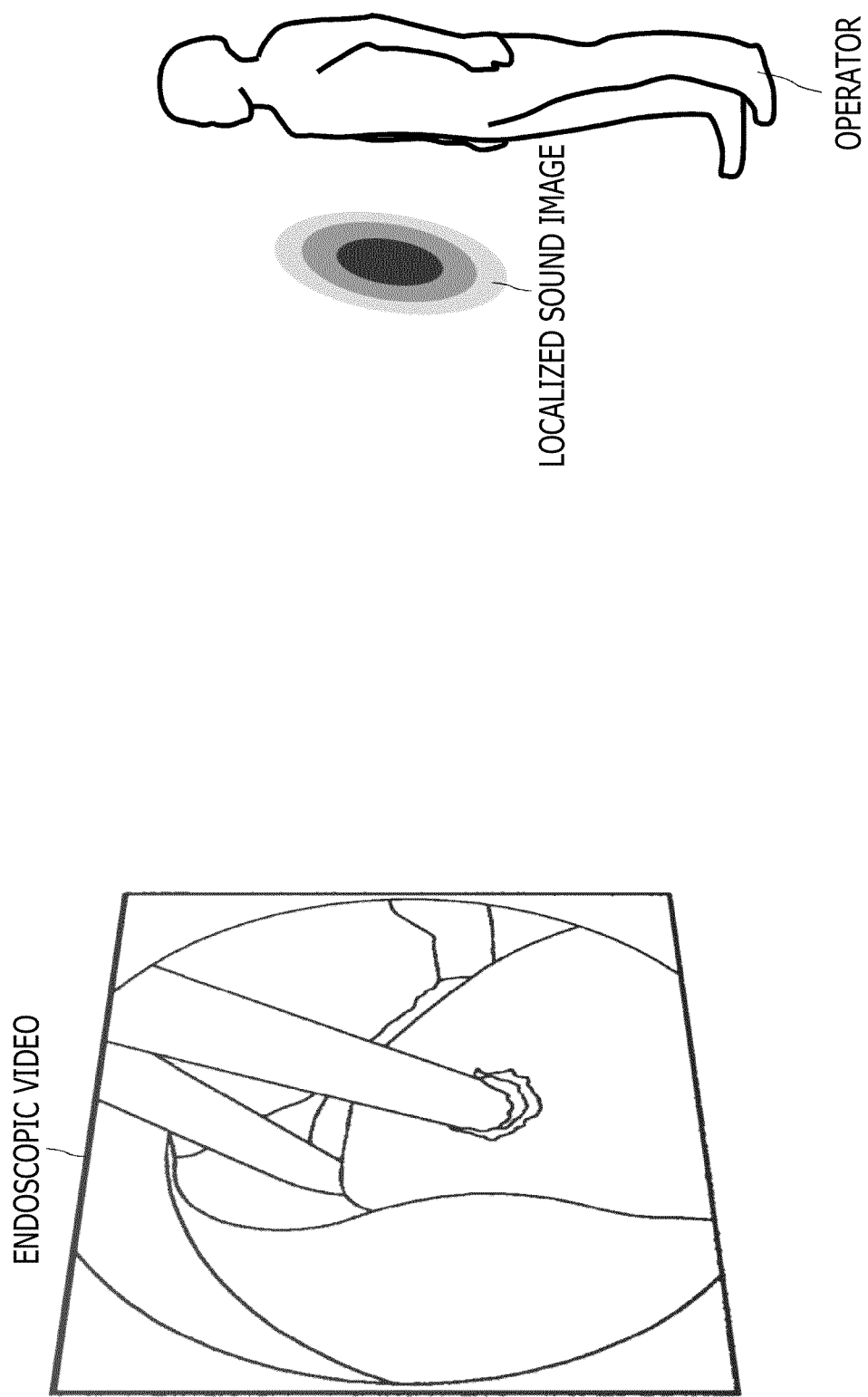
FIG. 15 is a diagram illustrating a state of localizing the sound image of the warning sound on the screen of the endoscopic video displaying the surgery site.

In a medical site equipped with the operating room system 1200, the surgery may be conducted while, for example, part of the body (such as a surgery site) of the patient is displayed on the screens of the display apparatuses 1203A to D. In this case, the sound image of the sound corresponding to the position of the surgery site displayed on the screen may be output and localized at the position corresponding to the display position of the surgery site on the screen. For example, when the surgery site on the screen of the endoscopic video is bleeding as illustrated in FIG. 13, a sound image of warning sound is localized at the position corresponding to the bleeding surgery site. In addition, the localized position of the sound image may be three-dimensionally changed between the operator and the screen based on three-dimensional depth information of the surgery site. For example, in a case where the depth of the bleeding position of the surgery site displayed on the screen is deep as illustrated in FIG. 14, the sound image is localized at a position closer to the screen (or a position farther from the operator). Conversely, in a case where the bleeding position is shallow, the sound image is localized at a position closer to the operator as illustrated in FIG. 15. The present technique can be used to appropriately draw the attention of the operator to the surgery site that needs to be treated quickly.

The images regarding the surgery site are obtained by the ceiling camera 1287 or the endoscope. In addition, the technique according to the present disclosure can be applied to the images of the operating room captured by the operating room camera 1289, and obviously, the technique can similarly be applied to images captured by other cameras, images captured in the past, and images delivered from the outside of the operating room.

Further, the present technique can also be applied to a surgery site existing outside of the screens of the display apparatuses 1203A to D. For example, although it is assumed that the surgery site displayed on the screens of the display apparatuses 1203A to D is part of the entire surgery site, there may be bleeding or the like from a surgery site not displayed on the screens during surgery. According to the present technique, the sound image of the warning sound can be localized according to the surgery site not displayed on the screens.

Figure 16:
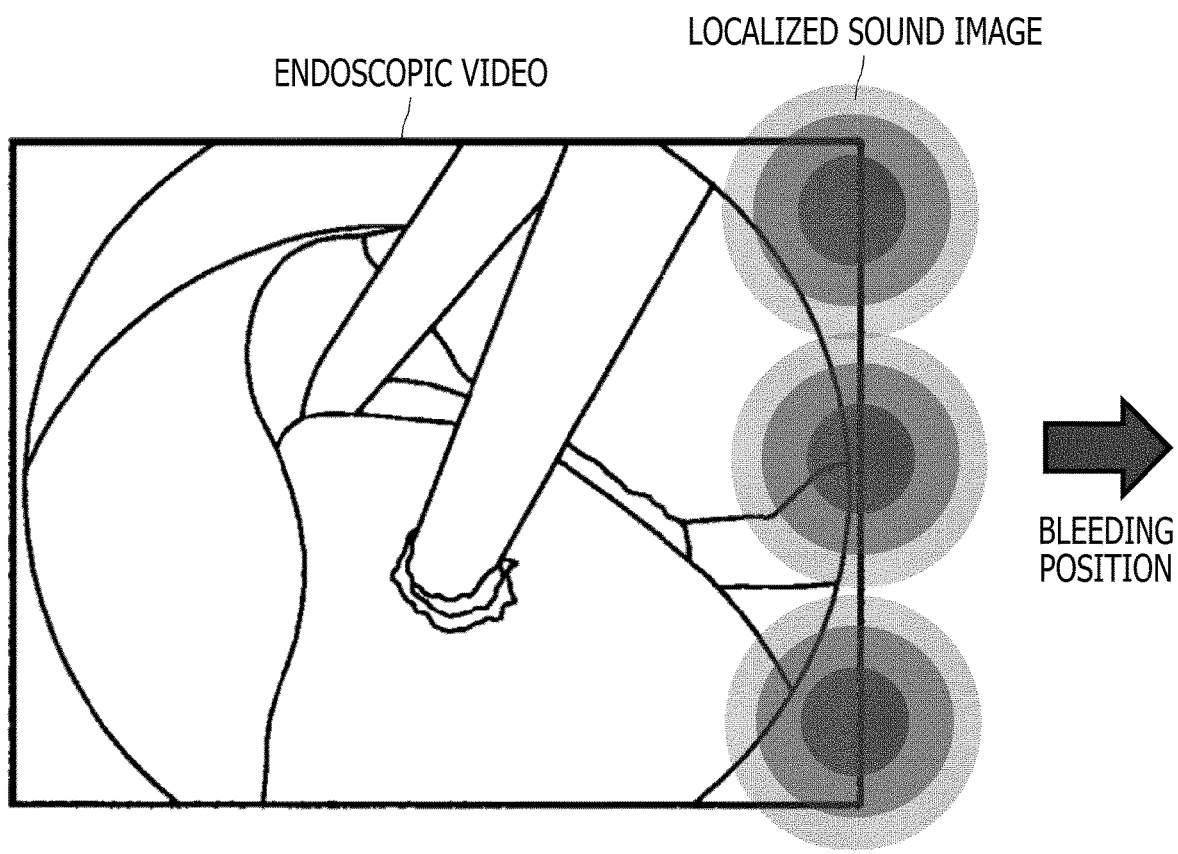
FIG. 16 is a diagram illustrating a state of localizing sound images of the warning sound on the screen of the endoscopic video displaying the surgery site.

In the case where there is bleeding from the surgery site existing outside of the screens of the display apparatuses 1203A to D, the sound image can be localized in the direction corresponding to the surgery site to draw the attention of the operator. For example, in a case where there is bleeding from the right-hand side of the surgery site displayed on the screen, the localization of the sound image is realized such that the warning sound can be heard from the right side of the screen as illustrated in FIG. 16. Here, the localization of the sound image on the right side of the screen may be localization of the sound image on the right side of the range of the screen of the display apparatus in the case where a general speaker system is adopted or may be localization of the sound image so as to generate the sound from the right half of the screen or from the right end of the screen in the case where the screen vibration speaker system with vibrators (see FIG. 11) is adopted. Further, in a case where plural speaker systems are combined and used, plural sound field generation methods may be combined and used.

In the case where the surgery site is outside of the range of the display screen, the technique according to the present disclosure can be applied to localize the sound image of the warning sound in any direction, and in addition, the localized position of the sound image may be changed according to the distance from the display range to the surgery site on the screen. For example, in a case where the distance from the display range to the surgery site on the screen is large, the sound image may be localized such that the sound is heard from farther than in a case where the distance is small. In addition, the volume of the output sound may be changed according to the distance from the display range to the surgery site on the screen. In this case, in the case where the distance from the display range to the surgery site on the screen is large, the generated sound may be larger than in the case where the distance is small.

In addition, the technique according to the present disclosure may be used along with display for drawing attention of the operator to the screens of the display apparatuses 1203A to D. An example of the display for drawing attention of the operator includes display of Graphic User Interface (GUI) indicating the direction from the display range on the screen to the surgery site. The GUI may include only simple display, such as an arrow symbol indicating the direction of the surgery site, or may also include description of information regarding the position and the direction of the surgery site.

Example 2

The technique according to the present disclosure can also be applied to an apparatus mounted on a type of moving body, such as a car, an electric car, a hybrid electric car, a motorcycle, a bicycle, a personal mobility, an airplane, a drone, a ship, a robot, a construction machine, and an agricultural machine (tractor). A case of applying the technique according to the present disclosure to a moving body control system will be described below.

Figure 17:
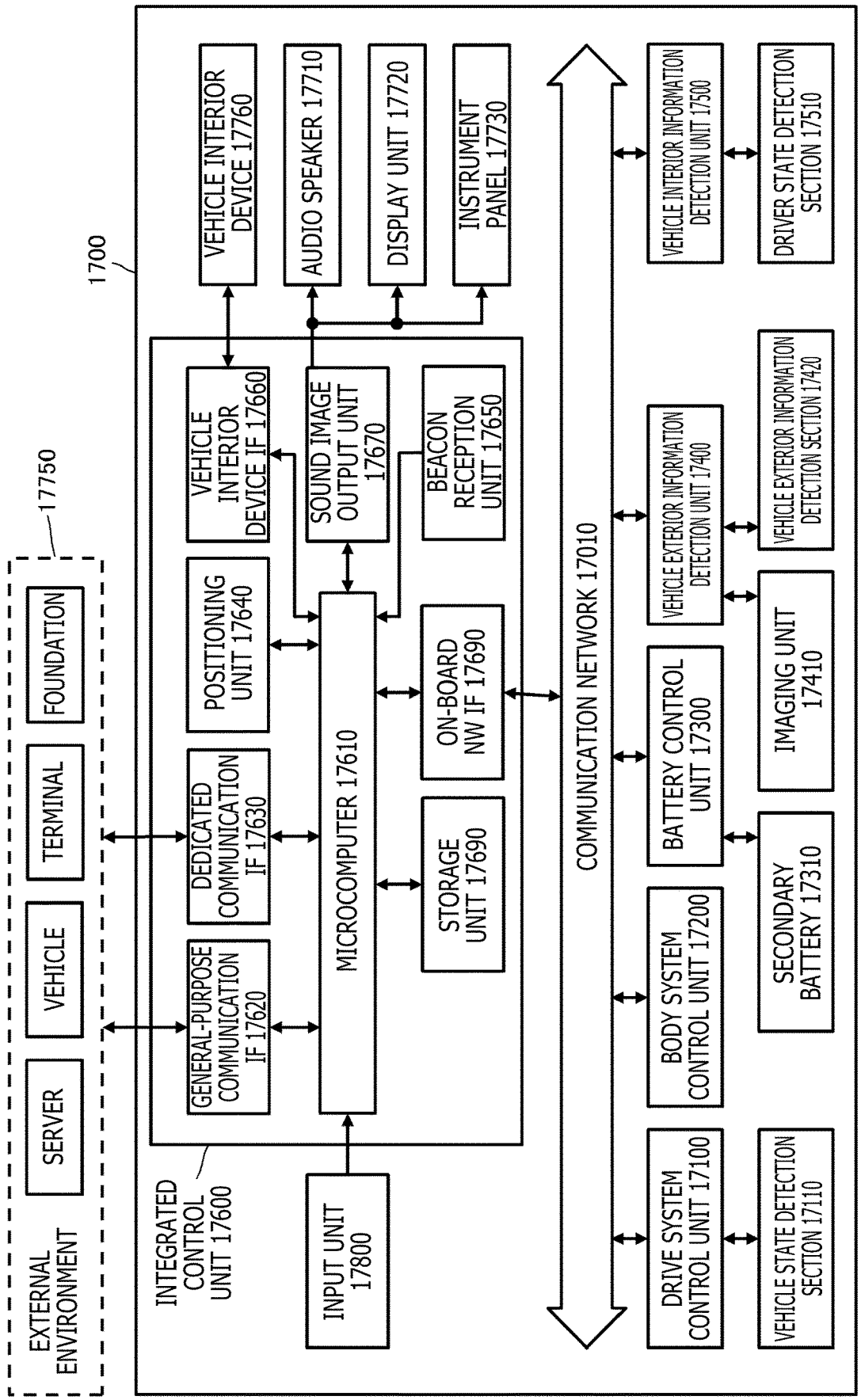
FIG. 17 is a diagram illustrating a schematic configuration example of a vehicle control system 1700.

FIG. 17 illustrates a schematic configuration example of a vehicle control system 1700 as an example of the moving body control system to which the technique according to the present disclosure can be applied. The illustrated vehicle control system 1700 includes a drive system control unit 17100, a body system control unit 17200, a battery control unit 17300, a vehicle exterior information detection unit 17400, a vehicle interior information detection unit 17500, and an integrated control unit 17600. A communication network 17010 connecting the plurality of control units includes, for example, an on-board communication network in compliance with any network, such as CAN (Controller Area Network), LIN (Local Interconnect Network), LAN (Local Area Network), and FlexRay (registered trademark).

Each control unit includes a microcomputer that executes arithmetic processing according to various programs, a storage unit that stores programs executed by the microcomputer, parameters used for various arithmetic operations, and the like, and a drive circuit that drives an apparatus to be controlled in various ways. Each control unit includes a network interface (IF) for communication with other control units through the communication network 17010 and includes a communication interface (IF) for communication with apparatuses or sensors inside and outside of the vehicle through wired communication or wireless communication. FIG. 17 illustrates functional components of the integrated control unit 17600 including a microcomputer 17610, a general-purpose communication interface (IF) 17620, a dedicated communication interface (IF) 17630, a positioning unit 17640, a beacon reception unit 17650, a vehicle interior device interface (IF) 17660, a sound image output unit 17670, an on-board network interface (NW IF) 17680, and a storage unit 17690. The other control units similarly include microcomputers, communication interfaces, storage units, and the like.

The drive system control unit 17100 controls actions of apparatuses related to the drive system of the vehicle according to various programs. For example, the drive system control unit 17100 functions as a control apparatus of a driving force generation apparatus, such as an internal combustion engine and a driving motor, that generates driving force of the vehicle, a driving force transmission mechanism that transmits the driving force to the wheel, a steering mechanism that adjusts the steering angle of the vehicle, a braking apparatus that generates braking force of the vehicle, and the like. The drive system control unit 17100 may have a function of a control apparatus of ABS (Antilock Brake System), ESC (Electronic Stability Control), or the like.

A vehicle state detection section 17110 is connected to the drive system control unit 17100. The vehicle state detection section 17110 includes, for example, at least one of a gyrosensor that detects the angular velocity of the axial rotation motion of the vehicle body, an acceleration sensor that detects the acceleration of the vehicle, or sensors for detecting the amount of operation of the accelerator pedal, the amount of operation of the brake pedal, the steering angle of the steering wheel, the engine speed, the rotational speed of the wheel, and the like. The drive system control unit 17100 uses signals input from the vehicle state detection section 17110 to execute arithmetic processing and control the internal combustion engine, the driving motor, the electric power steering apparatus, the braking apparatus, and the like.

The body system control unit 17200 controls actions of various apparatuses equipped on the vehicle body according to various programs. For example, the body system control unit 17200 functions as a control apparatus of a keyless entry system, a smart key system, a power window apparatus, and various lamps, such as a headlamp, a back lamp, a brake lamp, a turn signal, and a fog lamp. In this case, radio waves transmitted from a portable device substituting the key or signals of various switches may be input to the body system control unit 17200. The body system control unit 17200 receives input of the radio waves or the signals to control the door lock apparatus, the power window apparatus, the lamps, and the like of the vehicle.

The battery control unit 17300 controls a secondary battery 17310 that is a power supply source of the driving motor according to various programs. For example, information, such as battery temperature, battery output voltage, and remaining capacity of battery, is input to the battery control unit 17300 from a battery apparatus including the secondary battery 17310. The battery control unit 17300 uses these signals to execute arithmetic processing to control the temperature adjustment of the secondary battery 17310 or to control a cooling apparatus or the like included in the battery apparatus.

The vehicle exterior information detection unit 17400 detects information of the outside of the vehicle provided with the vehicle control system 1700. For example, at least one of an imaging unit 17410 or a vehicle exterior information detection section 17420 is connected to the vehicle exterior information detection unit 17400. The imaging unit 17410 includes at least one of a ToF (Time Of Flight) camera, a stereo camera, a monocular camera, an infrared camera, or other cameras. The vehicle exterior information detection section 17420 includes, for example, at least one of an environment sensor that detects the current weather or climate conditions or a surrounding information detection sensor that detects other vehicles, obstacles, pedestrians, and the like around the vehicle provided with the vehicle control system 1700.

The environment sensor may include, for example, at least one of a rain sensor that detects rainy weather, a fog sensor that detects fog, a sunlight sensor that detects the degree of sunlight, or a snow sensor that detects a snowfall. The surrounding information detection sensor may include at least one of an ultrasonic sensor, a radar apparatus, or a LIDAR (Light Detection and Ranging, Laser Imaging Detection and Ranging) apparatus. The imaging unit 17410 and the vehicle exterior information detection section 17420 may be provided as independent sensor and apparatus or may be provided as an integrated apparatus including a plurality of sensors and apparatuses.

Figure 18:
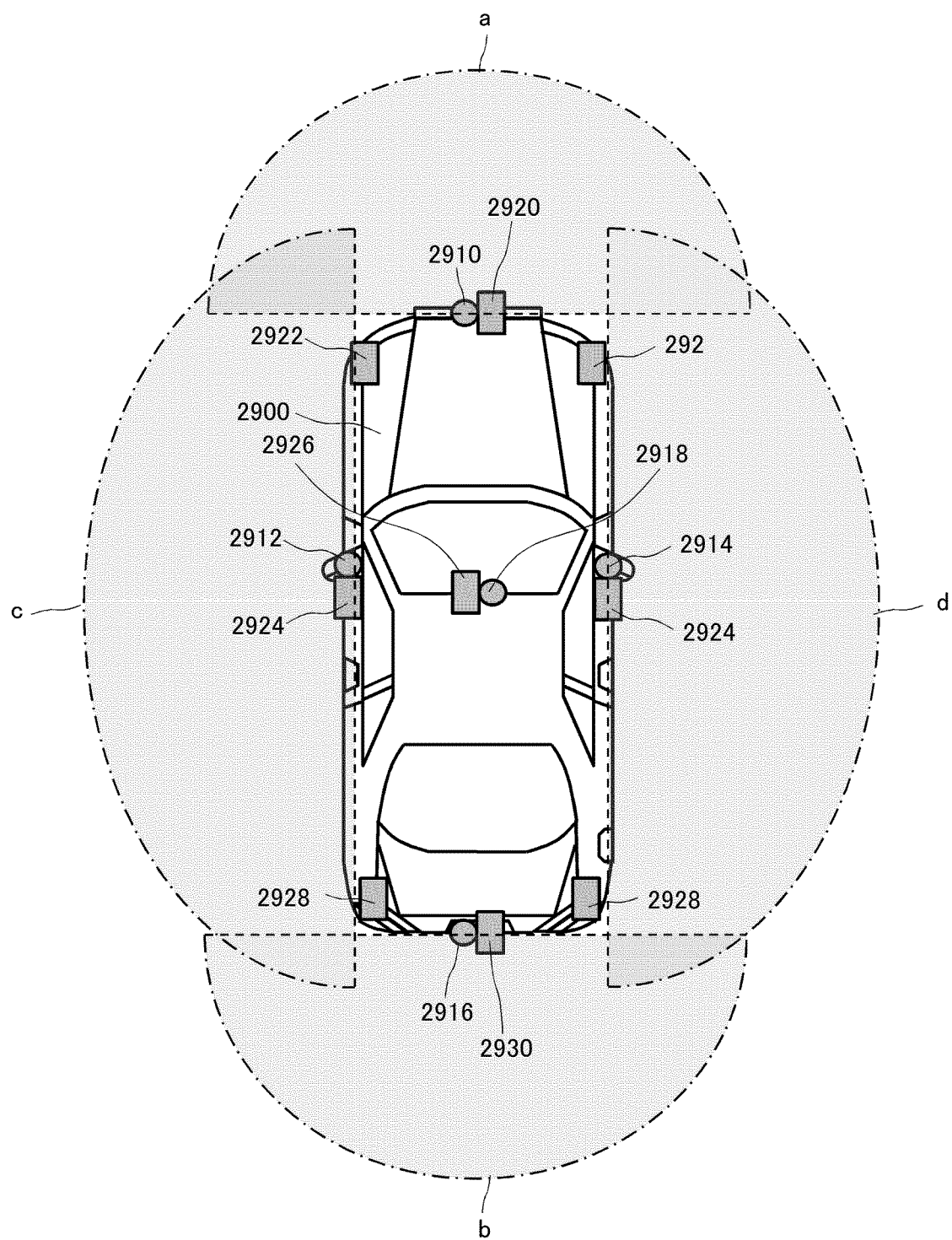
FIG. 18 is a diagram illustrating an example of installation positions of an imaging unit 17410 and a vehicle exterior information detection section 17420.

FIG. 18 illustrates an example of the installation positions of the imaging unit 17410 and the vehicle exterior information detection section 17420. Imaging units 2910, 2912, 2914, 2916, and 2918 are provided on at least one of the positions including, for example, the front nose, the side mirrors, the rear bumper, the back door, and the upper part of the windshield of the vehicle interior of a vehicle 2900. The imaging unit 2910 provided on the front nose and the imaging unit 2918 provided on the upper part of the windshield of the vehicle interior mainly acquire images in front of the vehicle 2900. The imaging units 2912 and 2914 provided on the side mirrors mainly acquire images on the left side and the right side of the vehicle 2900, respectively. The imaging unit 2916 provided on the rear bumper or the back door mainly acquires images behind the vehicle 2900. The imaging unit 2918 provided on the upper part of the windshield of the vehicle interior is mainly used to detect preceding vehicles, pedestrians, obstacles, traffic lights, traffic signs, driving lanes, and the like.

Note that FIG. 18 also illustrates an example of imaging ranges of the imaging units 2910, 2912, 2914, and 2916. An imaging range a indicates the imaging range of the imaging unit 2910 provided on the front nose. Imaging ranges b and c indicate the imaging ranges of the imaging units 2912 and 2914 provided on the side mirrors, respectively. The imaging range d indicates the imaging range of the imaging unit 2916 provided on the rear bumper or the back door. For example, a synthesizing process can be applied to image data captured by the imaging units 2910, 2912, 2914, and 2916 to obtain a bird's-eye image of the vehicle 2900 as viewed from above.

Vehicle exterior information detection sections 2920, 2922, 2924, 2926, 2928, and 2930 provided on the front, the rear, the side, the corner, and the upper part of the windshield of the vehicle interior of the vehicle 2900 include, for example, ultrasonic sensors or radar apparatuses. The vehicle exterior information detection sections 2920, 2926, and 2930 provided on the front nose, the rear bumper, the back door, and the upper part of the windshield of the vehicle interior of the vehicle 2900 include, for example, LIDAR apparatuses. The vehicle exterior information detection sections 2920 to 2930 are mainly used to detect preceding vehicles, pedestrians, obstacles, and the like.

The vehicle control system 1700 will continuously be described with reference again to FIG. 17. The vehicle exterior information detection unit 17400 causes the imaging unit 17410 to capture an image outside of the vehicle and receives the captured image data. In addition, the vehicle exterior information detection unit 17400 receives detection information from the connected vehicle exterior information detection section 17420. In a case where the vehicle exterior information detection section 17420 is an ultrasonic sensor, a radar apparatus, or a LIDAR apparatus, the vehicle exterior information detection unit 17400 causes the vehicle exterior information detection section 17420 to transmit an ultrasonic wave, an electromagnetic wave, or the like and receives information of the received reflected wave. Further, the vehicle exterior information detection unit 17400 can execute an object detection process or a distance detection process of persons, cars, obstacles, signs, characters on the road surface, and the like based on the received information. In addition, the vehicle exterior information detection unit 17400 can execute an environment recognition process of recognizing rain, fog, road surface conditions, and the like based on the received information. Further, the vehicle exterior information detection unit 17400 can calculate the distance to the objects outside of the vehicle based on the received information.

In addition, the vehicle exterior information detection unit 17400 may execute an image recognition process or a distance detection process of recognizing persons, cars, obstacles, signs, characters on the road surface, and the like based on the received image data. The vehicle exterior information detection unit 17400 may apply a process, such as distortion correction or position adjustment, to the received image data and combine image data captured by different imaging units 17410 to generate a bird's-eye image or a panoramic image. The vehicle exterior information detection unit 17400 may use the image data captured by different imaging units 17410 to execute a visual point conversion process.

The vehicle interior information detection unit 17500 detects information of the inside of the vehicle. For example, a driver state detection section 17510 that detects the state of the driver is connected to the vehicle interior information detection unit 17500. The driver state detection section 17510 includes a camera that images the driver, a biosensor that detects biometric information of the driver, a microphone that collects sound of the vehicle interior, and the like. The biosensor is provided on, for example, the seat surface, the steering wheel, or the like and detects the biometric information of an occupant sitting on a seat or the driver holding the steering wheel. The vehicle interior information detection unit 17500 may calculate the degree of fatigue or the degree of concentration of the driver or may determine whether or not the driver is dozing based on the detection information input from the driver state detection section 17510. The vehicle interior information detection unit 17500 may apply a process, such as a noise canceling process, to the collected sound signal.

The integrated control unit 17600 controls the entire actions in the vehicle control system 1700 according to various programs. An input unit 17800 is connected to the integrated control unit 17600. The input unit 17800 is realized by, for example, an apparatus, such as a touch panel, a button, a microphone, a switch, and a lever, that allows the occupant to perform an input operation. Data obtained by sound recognition of the sound input through the microphone may be input to the integrated control unit 17600.

In addition, the input unit 17800 may be, for example, a remote control apparatus using infrared rays or other radio waves or may be an external connection device, such as a portable phone and a PDA (Personal Digital Assistant), corresponding to the operation of the vehicle control system 1700.

In addition, the input unit 17800 may be, for example, a camera, and in that case, the occupant can input information through a gesture. Alternatively, data obtained by detecting the motion of a wearable apparatus worn by the occupant may be input to the integrated control unit 17600.

Further, the input unit 17800 may include, for example, an input control circuit or the like that generates an input signal based on information input by the occupant or the like using the input unit 17800 and that outputs the input signal to the integrated control unit 17600. The occupant or the like operates the input unit 17800 to input various types of data to the vehicle control system 1700 or instruct a processing operation.

The storage unit 17690 may include a ROM (Read Only Memory) that stores various programs executed by a microcomputer and a RAM (Random Access Memory) that stores various parameters, results of arithmetic operations, sensor values, and the like. In addition, the storage unit 17690 may include a magnetic storage device, such as an HDD (Hard Disc Drive), a semiconductor storage device, an optical storage device, a magneto-optical storage device, or the like.

A general-purpose communication interface 17620 is a versatile communication interface that mediates communication with various devices existing in an external environment 17750. The general-purpose communication interface 17620 may be provided with a cellular communication protocol, such as GSM (registered trademark) (Global System of Mobile communications), WiMAX (registered trademark), LTE (registered trademark) (Long Term Evolution), and LTE-A (LTE-Advanced), or other wireless communication protocols, such as wireless LAN (also referred to as Wi-Fi (registered trademark)) and Bluetooth (registered trademark). The general-purpose communication interface 17620 may connect to a device (for example, application server or control server) existing on an external network (for example, Internet, cloud network, or network specific to business) through, for example, a base station or an access point. In addition, the general-purpose communication interface 17620 may use, for example, a P2P (Peer To Peer) technique to connect to a terminal existing near the vehicle (for example, terminal of driver, pedestrian, or shop or MTC (Machine Type Communication) terminal).

The dedicated communication interface 17630 is a communication interface that supports the communication protocol established to be used in the vehicle. The dedicated communication interface 17630 is provided with, for example, a standard protocol, such as WAVE (Wireless Access in Vehicle Environment) that is a combination of IEEE 802.11p in a lower layer and IEEE 1609 in an upper layer, DSRC (Dedicated Short Range Communications), and a cellular communication protocol. The dedicated communication interface 17630 typically conducts V2X communication that is a concept including at least one of vehicle-to-vehicle (Vehicle to Vehicle) communication, vehicle-to-infrastructure (Vehicle to Infrastructure) communication, vehicle-to-home (vehicle to Home) communication, or vehicle-to-pedestrian (Vehicle to Pedestrian) communication.

The positioning unit 17640 receives, for example, a GNSS (Global Navigation Satellite System) signal (for example, GPS signal from GPS (Global Positioning System) satellite) from a GNSS satellite to execute position measurement and generates position information including the latitude, the longitude, and the altitude of the vehicle. Note that the positioning unit 17640 may exchange a signal with a wireless access point to specify the current position or may acquire the position information from a terminal with positioning function, such as a portable phone, a PHS (Personal Handy-phone System), and a smartphone.

The beacon reception unit 17650 receives a radio wave or an electromagnetic wave transmitted from, for example, a wireless station or the like installed on the road and acquires information of the current position, traffic jam, road closed, required time, and the like. Note that the function of the beacon reception unit 17650 may be included in the dedicated communication interface 17630.

The vehicle interior device interface 17660 is a communication interface that mediates connection between the microcomputer 17610 and various vehicle interior devices 17760 existing inside of the vehicle. The vehicle interior device interface 17660 may use a wireless communication protocol, such as wireless LAN, Bluetooth (registered trademark), NFC (Near Field Communication), and WUSB (Wireless USB), to establish wireless communication. In addition, the vehicle interior device interface 17660 may establish wired communication, such as USB, HDMI (registered trademark), and MHL (Mobile High-definition Link), through a connection terminal not illustrated (and a cable if necessary). The vehicle interior device 17760 may include, for example, at least one of a mobile device or a wearable device possessed by the occupant or an information device carried in or attached to the vehicle. In addition, the vehicle interior device 17760 may include a navigation apparatus that searches for a route to any destination. The vehicle interior device interface 17660 exchanges control signals or data signals with the vehicle interior devices 17760.

The on-board network interface 17680 is an interface that mediates communication between the microcomputer 17610 and the communication network 17010. The on-board network interface 17680 transmits and receives signals and the like according to a predetermined protocol supported by the communication network 17010.

The microcomputer 17610 in the integrated control unit 17600 controls the vehicle control system 1700 according to various programs based on the information acquired through at least one of the general-purpose communication interface 17620, the dedicated communication interface 17630, the positioning unit 17640, the beacon reception unit 17650, the vehicle interior device interface 17660, or the on-board network interface 17680. For example, the microcomputer 17610 may compute a control target value of the driving force generation apparatus, the steering mechanism, or the braking apparatus based on the acquired information inside and outside of the vehicle and output a control command to the drive system control unit 17100. Specifically, the microcomputer 17610 may perform cooperative control for realizing functions of ADAS (Advanced Driver Assistance System) including avoidance of collision or shock mitigation of vehicle, follow-up traveling based on the following distance, traveling at a constant speed, collision warning of vehicle, lane departure warning of vehicle, and the like. In addition, the microcomputer 17610 may control the driving force generation apparatus, the steering mechanism, the braking apparatus, or the like based on the acquired information around the vehicle to perform cooperative control for automatic drive or the like for autonomous traveling regardless of the operation of the driver.

The microcomputer 17610 may generate three-dimensional distance information between the vehicle and objects, such as surrounding structures and people, to create local map information including peripheral information of the current position of the vehicle based on the information acquired through at least one of the general-purpose communication interface 17620, the dedicated communication interface 17630, the positioning unit 17640, the beacon reception unit 17650, the vehicle interior device interface 17660, or the on-board network interface 17680. In addition, the microcomputer 17610 may predict danger, such as collision of vehicle, approach of pedestrian or the like, and entry into road closed, to generate a warning signal based on the acquired information. The warning signal may be, for example, a signal for generating warning sound or for lighting a warning lamp.

The sound image output unit 17670 transmits an output signal of at least one of sound or image to an output apparatus that can visually or aurally transmit information to the occupant of the vehicle or to the outside of the vehicle. In the example illustrated in FIG. 17, an audio speaker 17710, a display unit 17720, and an instrument panel 17730 are provided as output apparatuses. The display unit 17720 may include, for example, at least one of an on-bard display or a head-up display. The display unit 7720 may be a display unit of a car navigation system. The display unit 17720 may have an AR (Augmented Reality) display function. The output apparatus may be an apparatus other than these apparatuses, such as a headphone, a wearable device including a head-mounted display worn by the occupant, a projector, and a lamp. A display apparatus as an output apparatus visually displays the results obtained by various processes executed by the microcomputer 17610 or the information received from other control units in various formats, such as text, image, table, and graph. In addition, a sound output apparatus as an output apparatus converts an audio signal including reproduced sound data, acoustic data, or the like into an analog signal and aurally outputs the analog signal.

Note that, in the vehicle control system 1700 illustrated in FIG. 17, at least two control units connected through the communication network 7010 may be integrated into one control unit. Alternatively, individual control units may include a plurality of control units. Further, the vehicle control system 1700 may include other control units not illustrated. In addition, part or all of the functions of one of the control units described above may be provided to another control unit. That is, predetermined arithmetic processing may be executed by any of the control units as long as the information is transmitted and received through the communication network 17010. Similarly, a sensor or an apparatus connected to one of the control units may be connected to another control unit, and a plurality of control units may mutually transmit and receive the detection information through the communication network 17010.

In the vehicle control system 1700 as described above, there may be, for example, a case in which information regarding other vehicles in the surroundings detected by the vehicle exterior information detection unit 17400 is displayed on the display unit 17720. In this case, the process of the microcomputer 17610 or the like can be executed to localize the sound image of the sound output from the audio speaker 17710 according to the relation between another vehicle displayed on the display unit 17720 and the vehicle provided with the vehicle exterior information detection unit 17400. Therefore, the technique according to the present disclosure can be used to appropriately draw the attention of the driver or the occupant to another vehicle or pedestrian through the localized position of the sound image.

Figure 19:
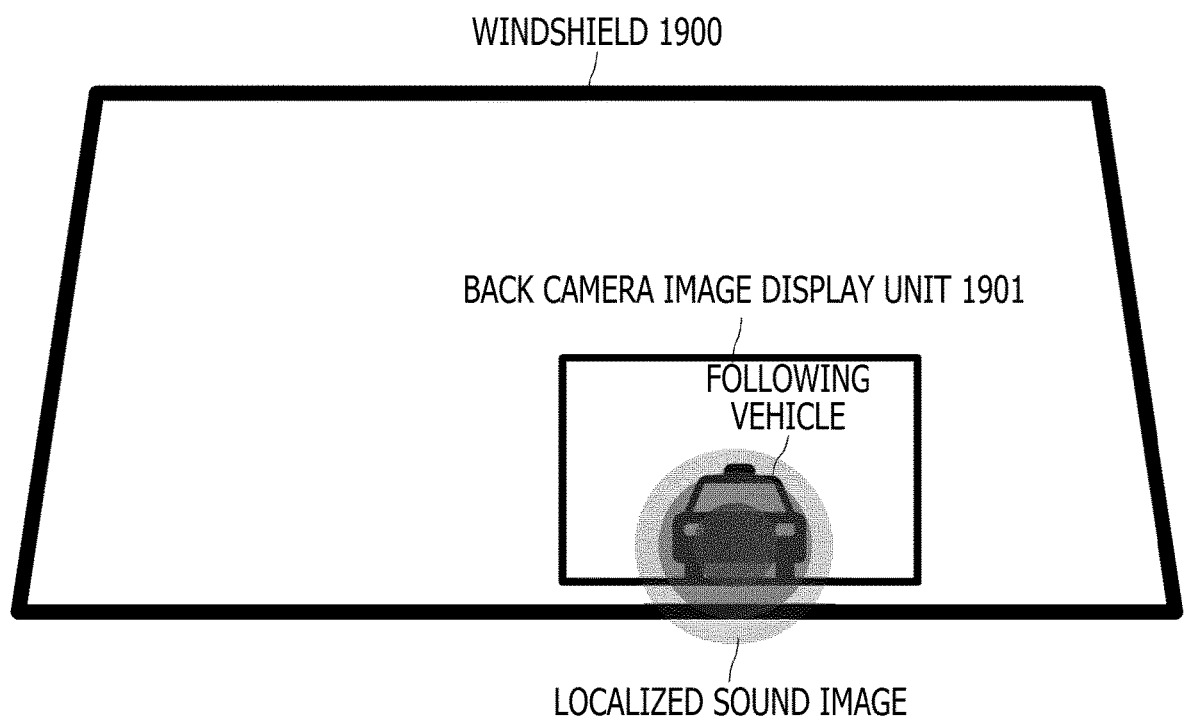
FIG. 19 is a diagram illustrating a specification example of sound localization in the vehicle control system 1700.
Figure 20:
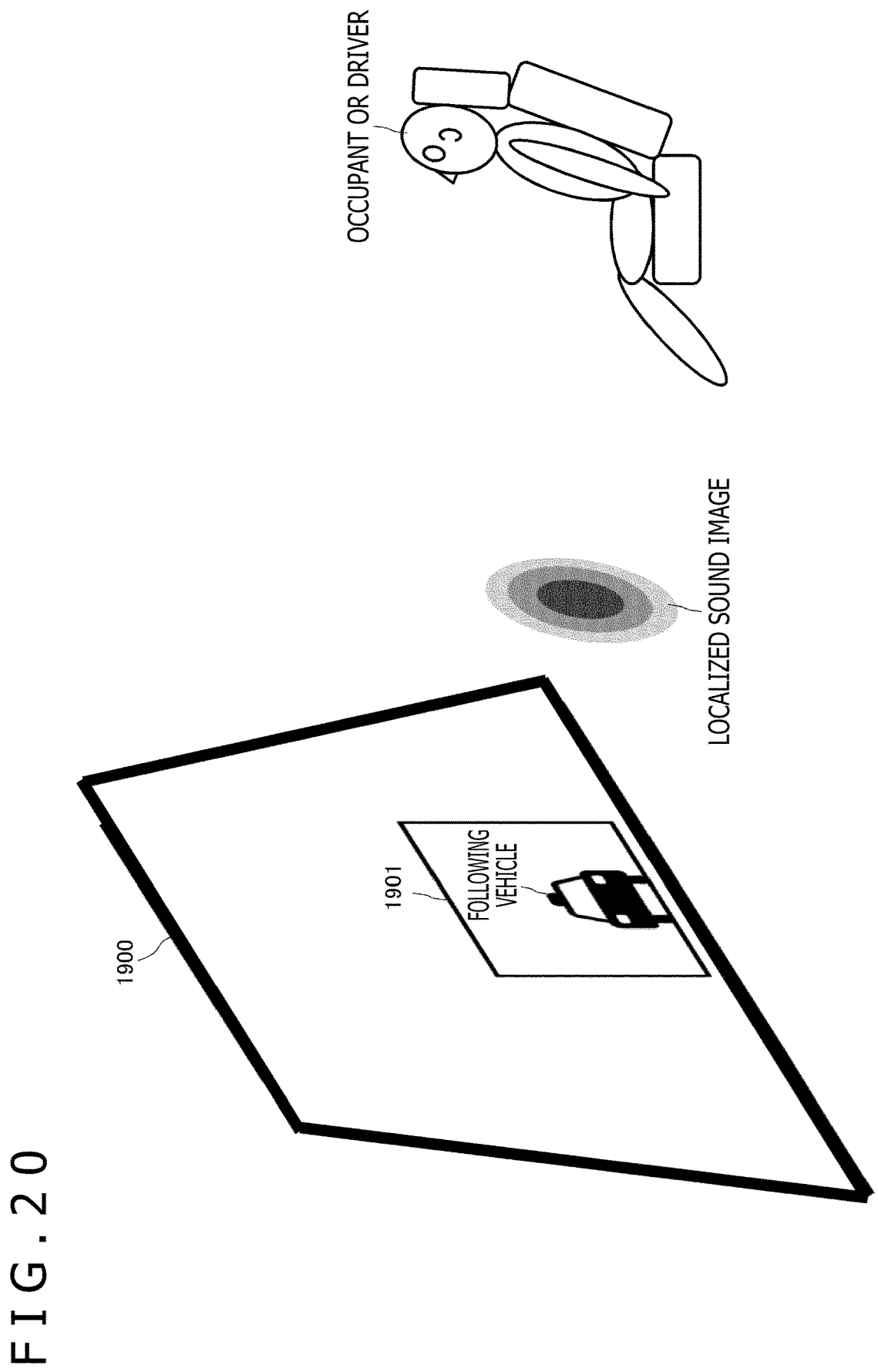
FIG. 20 is another diagram illustrating a specific example of the sound localization in the vehicle control system 1700.
Figure 21:
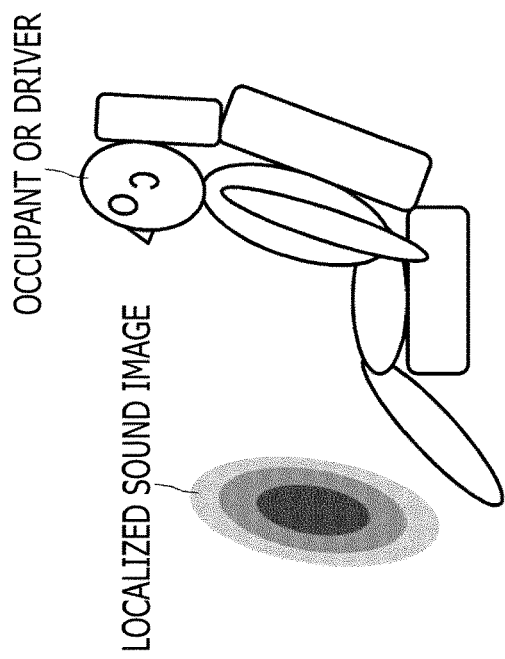
FIG. 21 is still another diagram illustrating a specific example of the sound localization in the vehicle control system 1700.
Figure 21:
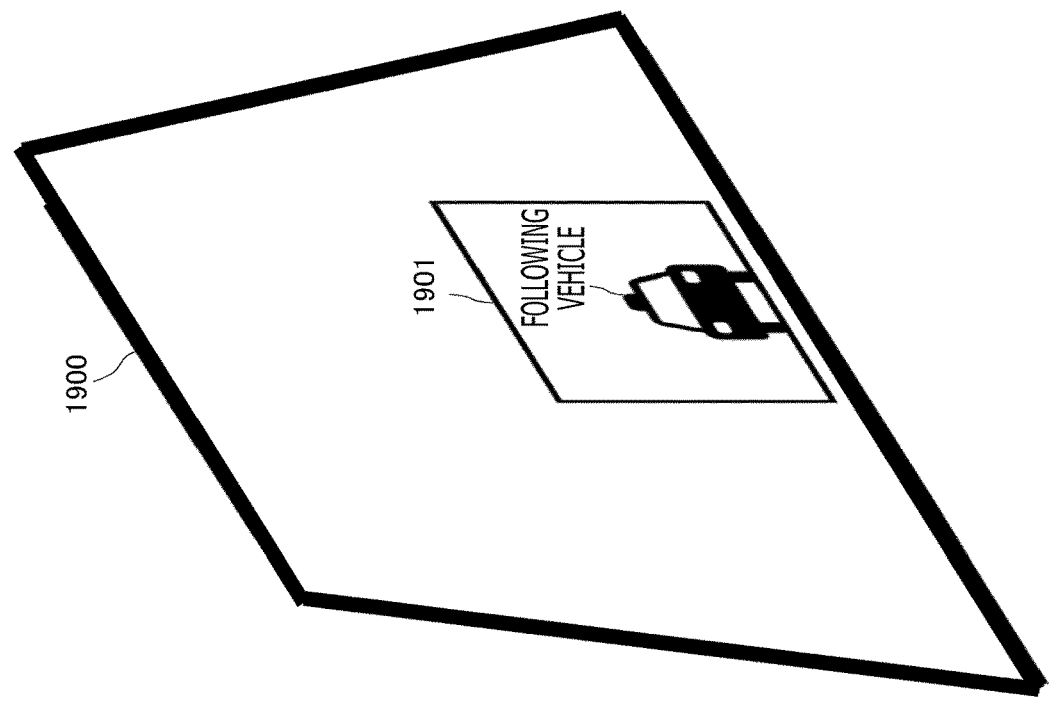

FIGS. 19 to 21 illustrate specific examples of the sound localization using the technique according to the present disclosure. In the example illustrated in FIG. 19, part of a windshield 1900 is allocated to the display unit 17720 that displays or projects an image. Further, the display unit 17720 in the windshield 1900 is used as a back camera image display unit 1901 that displays or projects an image captured by a back camera. As illustrated, when a following vehicle is displayed or projected to the back camera image display unit 1901, the sound image of sound, such as warning sound, is localized at the position corresponding to the display position of the following vehicle. In that case, the localized position of the sound image may be three-dimensionally changed between the driver or the occupant and the display unit 17720 according to the position and the speed of the following vehicle and the following distance from the vehicle to the following vehicle. In that case, the volume of the sound in localizing the sound image may also be controlled.

While applying the sound localization process to the display position of the following vehicle, the vehicle control system 1700 may use the driver state detection section 17510 to detect the position and the posture of the driver or the occupant inside of the vehicle and take into account the position and the posture of the driver or the occupant to control the localized position of the sound image. For example, in a case where the following distance between the vehicle and the following vehicle is large, the sound image of the sound is localized at a position closer to the screen as illustrated in FIG. 20 to aurally express that the following distance is large. Conversely, in a case where the following distance is small, the sound image is localized at a position closer to the driver or the occupant as illustrated in FIG. 21 to aurally express that the following distance is small.

Similarly, in a case where the travel speed of the following vehicle is smaller than the travel speed of the vehicle, the sound image of the sound is localized at a position closer to the screen. Conversely, in a case where the travel speed of the following vehicle is larger than the travel speed of the vehicle, the sound image of the sound is localized at a position closer to the driver or the occupant to aurally express the situation that the following vehicle is approaching the vehicle.

Note that the relation between the following vehicle and the localized position of the sound image as described above is just an example, and the relation is not limited to the example. For example, the sound localization may be controlled such that the sound image is localized at a position closer to the driver or the occupant in the case where the following distance between the following vehicle displayed on the screen and the vehicle is large, and the sound image is localized at a position closer to the screen in the case where the following distance is small. In addition, the volume of the output sound may be changed according to the relation between the vehicle and the following vehicle.

Although the case of controlling the localized position of the sound image according to the relation between the vehicle and the following vehicle has been described with reference to FIGS. 19 to 21, the technique according to the present disclosure is not limited to this. According to the technique of the present disclosure, the localized position of the sound image can also be controlled according to an object other than the following vehicle that can be detected by the vehicle exterior information detection unit 17400.

Figure 22:
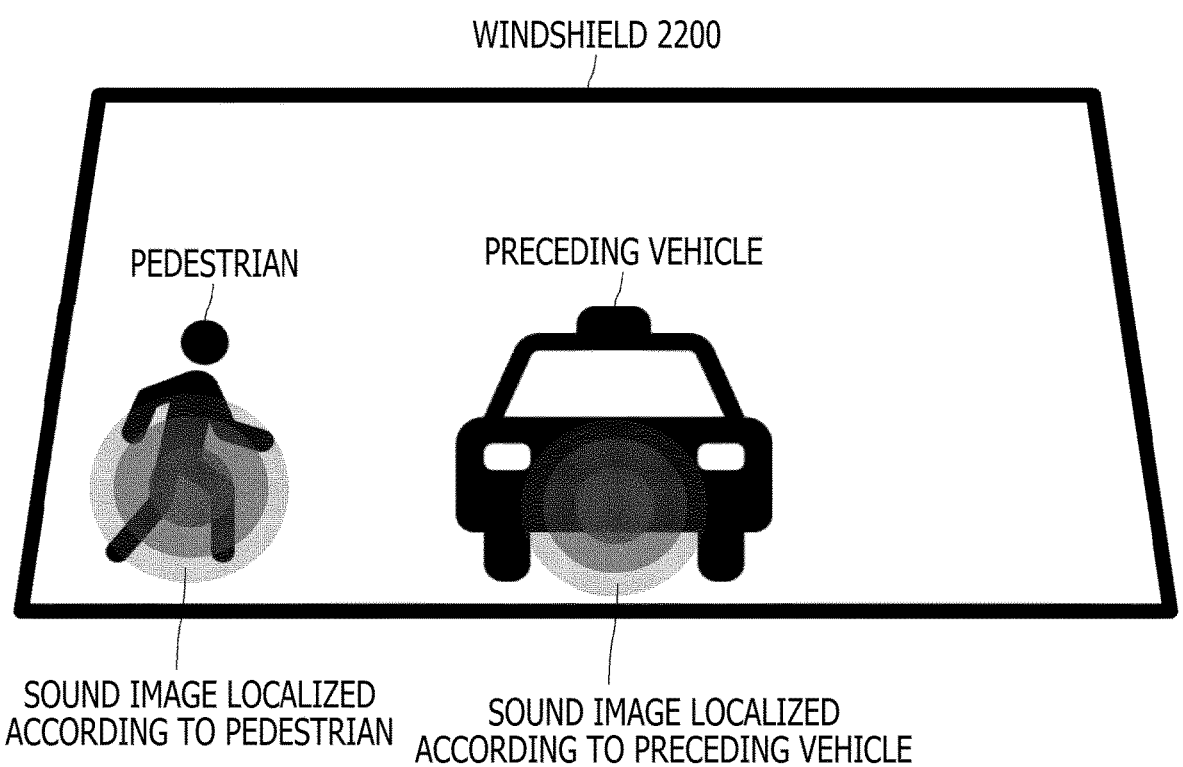
FIG. 22 is a diagram illustrating another specific example of the sound localization in the vehicle control system 1700.

FIG. 22 illustrates another specific example of the sound localization using the technique according to the present disclosure. In the example illustrated in FIG. 22, part of a windshield 2200 is allocated to the display unit 17720 that displays or projects an image. Further, the sound images of the sound corresponding to a pedestrian and a preceding vehicle positioned in front of the vehicle detected by the vehicle exterior information detection unit 17400 are localized on the display unit 17720 (or the windshield 2200).

As illustrated in FIG. 22, in a case where an object detected by the vehicle exterior information detection unit 17400 is positioned in front in the travel direction of the vehicle, the object may be visually recognized by the driver through the windshield 2200 in front of the driver. In such a case, the object positioned in front of the vehicle does not always have to be visually recognized by the driver through the display unit 17720. However, as in the case of the object positioned behind the vehicle (see FIGS. 19 to 21), the localized position of the sound image may be three-dimensionally changed between the windshield 2200 and the driver according to the position and the speed of the object in front and the distance from the vehicle to the object in front. In that case, the volume of the sound in localizing the sound image may also be controlled.

Note that a transmissive display can be used for the windshield 2200. In this case, there are an object visually recognized by the driver as transmitted light from the outside and an object visually recognized by the driver based on output light from the transmissive display. The sound image may be localized similarly for the object visually recognized as transmitted light and the object visually recognized as output light, or the method of localizing the sound image may vary depending on whether the object is an object based on the transmitted light or an object based on the output light. For example, for the image of the following car displayed on the windshield including the transmissive display, the sound image may be localized such that the sound is heard from the back.

Furthermore, in the case of applying the screen vibration speaker technique to a normal windshield or a windshield using a transmissive display, vibrators may be installed on the windshield, or the sound may be output such that the frame of the vehicle body vibrates the windshield. The technique using the screen vibration speaker can be applied not only to the windshield, but also to a side window or a rear window.

So far, the examples of three-dimensionally changing the localized position of the sound image between the display position of the object (such as following vehicle, preceding vehicle, and pedestrian) on the windshield as the display unit 17720 and the driver or the occupant have been described. On the other hand, the localized position of the sound image may be changed between the actual position of the object and the driver or the occupant.

Figure 23:
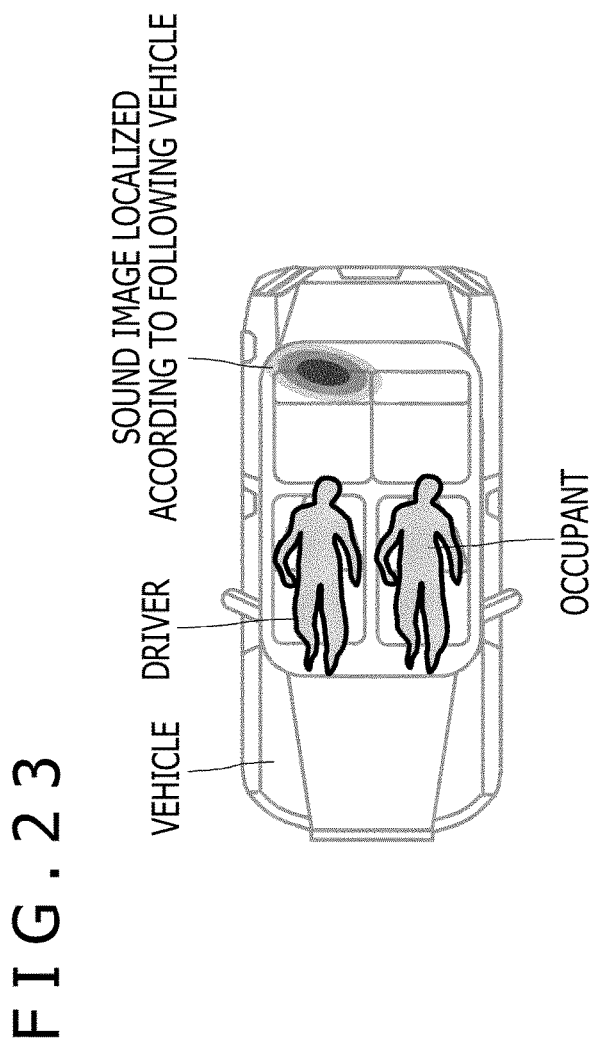
FIG. 23 is another diagram illustrating another specific example of the sound localization in the vehicle control system 1700.
Figure 24:
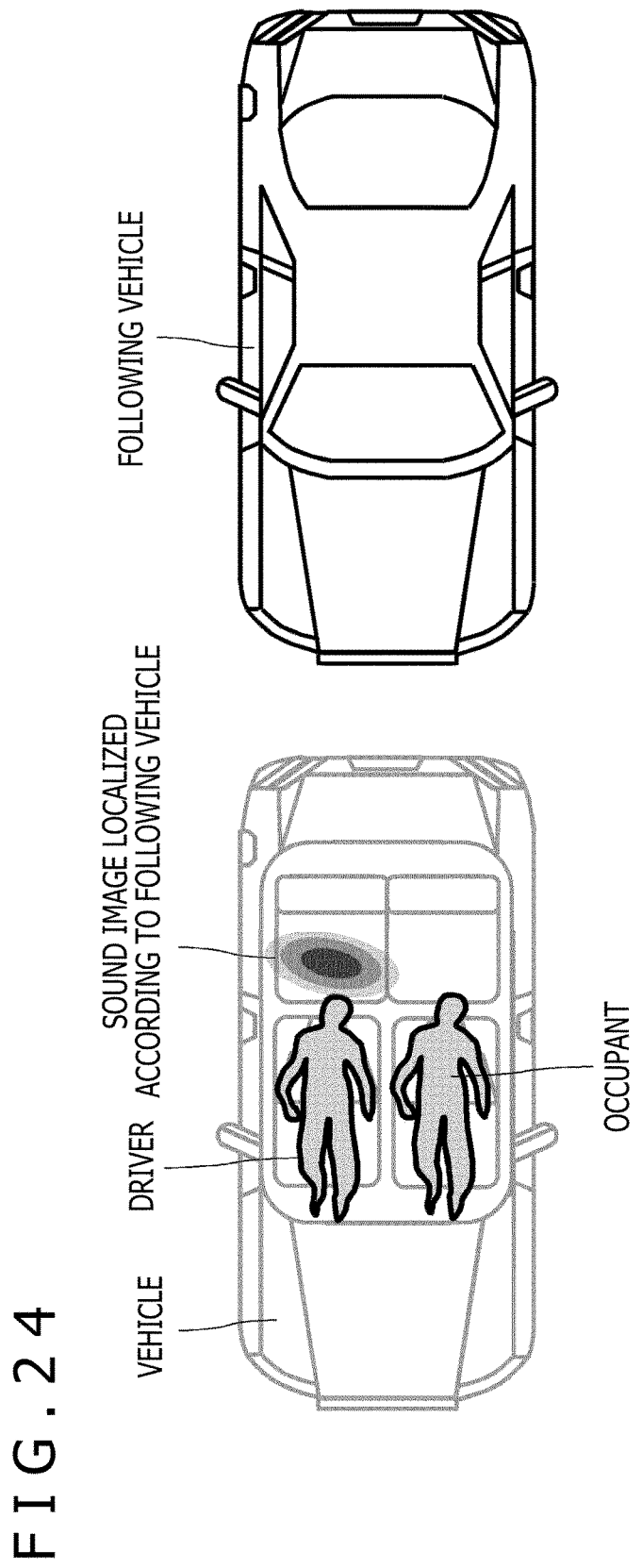
FIG. 24 is still another diagram illustrating another specific example of the sound localization in the vehicle control system 1700.

Specifically, the vehicle control system 1700 uses the vehicle exterior information detection unit 17400 to detect the following distance between the vehicle and the following vehicle and uses the driver state detection section 17510 to detect the position and the posture of the driver or the occupant inside of the vehicle and thereby three-dimensionally change the localized position of the sound image between the actual position of the following vehicle and the driver or the occupant. For example, in the case where the following distance between the vehicle and the following vehicle is large, the sound image of the sound is localized at a position closer to the following vehicle (for example, near the rear window) as illustrated in FIG. 23 to aurally express that the following distance is large. Conversely, in the case where the following distance is small, the sound image is localized at a position closer to the driver or the occupant (for example, near the back of the head) as illustrated in FIG. 24 to aurally express that the following distance is small.

Similarly, in the case where the travel speed of the following vehicle is smaller than the travel speed of the vehicle, the sound image of the sound is localized at a position closer to the following vehicle (for example, near the rear window). Conversely, in the case where the travel speed of the following vehicle is larger than the travel speed of the vehicle, the sound image of the sound is localized at a position closer to the driver or the occupant (for example, near the back of the head), and the situation that the following vehicle is approaching the vehicle is aurally expressed.

Note that the relations between the actual position of the following vehicle and the localized position of the sound image are just examples, and the relations are not limited to the examples. For example, the sound localization may be controlled such that the sound image is localized at a position closer to the driver or the occupant (for example, near the back of the head) in the case where the following distance between the following vehicle and the vehicle is large, and the sound image is localized at a position closer to the following vehicle (for example, near the rear window) in the case where the distance from the following vehicle is small. In addition, the volume of the output sound may be changed according to the relation between the vehicle and the following vehicle.

Example 3

Lastly, a case of applying and using the technique according to the present disclosure in the vehicle control system 1700 in which part or all of the windshield, the rear window, and the side windows are the display unit 17720 will be described. Here, the display unit 17720 may be a transmissive display using part or all of the windshield, the rear window, and the side windows.

For example, in a case where the vehicle provided with the vehicle control system 1700 is a self-driving car, the driver and the occupant can use part or all of the windshield, the rear window, and the side windows as the display unit 17720 to view the video content or browse the Internet during running or stopping of the vehicle. Further, the technique according to the present disclosure can be applied to localize the sound image and generate the sound field in cooperation with the display object displayed on the display unit 17720, and the sense of immersion into the content can be improved for the driver and the occupant. In this case, the information regarding the position and the posture of the driver or the occupant inside of the vehicle detected by the driver state detection section 17510 can be used to localize the sound image.

Specifically, in a case where all of the windshield, the rear window, and the side windows are the display unit 17720 and the screen vibration speaker technique using the vibrators is mounted, the sound image of the sound can be localized at the display position of the object in the corresponding content, and the display position can partially be vibrated to transmit the sound to the driver or the occupant.

Note that the multi-window (for example, see FIG. 1) can be applied to the display unit 17720 using part or all of the windshield, the rear window, and the side windows. In this case, each video, such as broadcast content, streaming content, visual communication, and graphics, is displayed on part or all of the windshield, the rear window, and the side windows. In addition, the multi-window may include a window for displaying the information (such as following vehicles, preceding vehicles, and pedestrians) acquired by the vehicle exterior information detection unit 17400.

Further, the processing function as illustrated in FIG. 9 can be provided on the vehicle control system 1700 to detect the position of the object displayed on each window to localize the sound image at an appropriate position according to the technique of the present disclosure. As illustrated in FIG. 9, the face position of the performer (speaker) in the window may be detected, and the sound image may be localized at the position corresponding to the face position of the performer (speaker). In addition, the sound image may be localized at the position corresponding to the object in the window corresponding to the object acquired by the vehicle exterior information detection unit 17400.

Although the description above is based on the assumption that the screen vibration speaker is used as the audio speaker 17710, a general speaker system may obviously be used, and the screen vibration speaker and another speaker system may also be combined and used. However, in the case where the screen vibration speaker is used, the general speaker system does not have to be arranged in the vehicle interior, and the space of the vehicle interior can effectively be utilized.

In addition, the description above is based on the assumption that part or all of the windshield, the rear window, and the side windows are the display unit 17720, and that the screen vibration speaker is used as the audio speaker 17710. However, the configuration for realizing the technique according to the present disclosure is not limited to this. For example, the light arranged on the ceiling of the vehicle interior may have a housing vibration speaker function using vibrators. In this way, the general speaker system does not have to be arranged in the vehicle interior, and the space of the vehicle interior can effectively be utilized.

INDUSTRIAL APPLICABILITY

The technique disclosed in the present specification has been described in detail with reference to the specific embodiment. However, it is apparent that those skilled in the art can modify or substitute the embodiment without departing from the scope of the technique disclosed in the present specification.

Although the embodiment applying the technique disclosed in the present specification to the television apparatus has mainly been described in the present specification, the scope of the technique disclosed in the present specification is not limited to this. The technique disclosed in the present specification can similarly be applied to various types of display apparatuses, such as a projector, a personal computer, a tablet, and a smartphone, that display videos and that output sound in synchronization with the videos.

In addition, the technique disclosed in the present specification can be more suitably operated by combining the technique with, for example, the screen vibration speaker technique.

In addition, the technique disclosed in the present specification can be applied to various products using displays and speakers. For example, the technique disclosed in the present specification can also be applied to an operating room system and a vehicle control system. Examples of the vehicle include a car, an electric car, a hybrid electric car, a motorcycle, a bicycle, a personal mobility, an airplane, an unmanned aerial vehicle, such as a drone, a walking or wheeled robot, a construction machine, and an agricultural machine (such as a tractor).

That is, the technique disclosed in the present invention has been described in a form of an example, and the description of the present specification should not be restrictively interpreted. The claims should be taken into account to determine the scope of the technique disclosed in the present specification.

Note that the technique disclosed in the present specification can also be configured as follows.

(1)

An information processing apparatus including:

a control section that detects a position of a sound source appearing in a video displayed on a screen of a display unit and that uses one or more vibrators to vibrate the display unit and thereby control output of sound such that a sound image of sound in synchronization with the video is localized at the position where the sound source appears on the screen displaying the video.

(2)

The information processing apparatus according to (1), in which the control section detects a sound source appearing in a video of broadcast or an OTT service or in an externally input video and localizes a sound image at the position where the sound source appears on the screen.

(3)

The information processing apparatus according to either one of (1) and (2), in which the control section detects a sound source appearing in a video of visual communication and localizes a sound image at the position where the sound source appears on the screen.

(4)

The information processing apparatus according to any one of (1) to (3), in which the control section detects, as a sound source, predetermined graphics displayed on the screen and localizes sound related to the graphics at a position where the graphics are displayed on the screen.

(5)

The information processing apparatus according to (4), in which the control section detects, as a sound source, graphics of a sound agent executed on the information processing apparatus and localizes a sound image of sound of the sound source at the position where the graphics are displayed on the screen.

(6)

The information processing apparatus according to (5), further including:

a detection section that detects a user interacting with the sound agent, in which the control section further controls a display position of the character according to a position of the user.

(7)

The information processing apparatus according to (4), in which the control section detects, as a sound source, graphics of OSD or UI appearing on the screen and localizes a sound image of a sound effect associated with the graphics in synchronization with display of the graphics on the screen.

(8)

The information processing apparatus according to any one of (1) to (7), in which in a case of displaying videos of two or more video sources on individual windows, the control section localizes a sound image of a sound source detected from the video of each video source at a position where the sound source appears in the corresponding window.

(9)

An information processing method including:

a detection step of detecting a position of a sound source appearing in a video displayed on a screen of a display unit; and a control step of using one or more vibrators to vibrate the display unit and thereby control output of sound such that a sound image of sound in synchronization with the video is localized at the position where the sound source appears on the screen displaying the video.

(10)

A video sound output system including:

a display unit;

a sound output unit that uses one or more vibrators to vibrate the display unit and thereby output sound; and a control section that detects a position of a sound source appearing in a video displayed on a screen of the display unit and that controls the sound output unit such that a sound image of sound in synchronization with the video is localized at the position where the sound source appears on the screen displaying the video.

REFERENCE SIGNS LIST

100 . . . Television apparatus
200 . . . Television apparatus (information processing apparatus)
201 . . . Processing unit, 202 . . . Tuner,
203 . . . Communication unit, 204 . . . Display unit
205 . . . Sound input unit, 206 . . . Sound output unit,
207 . . . Imaging unit
208 . . . Sensor unit, 209 . . . Remote control reception unit, 210 . . . Recording unit
301 . . . Video processing unit, 302 . . . Sound processing unit, 303 . . . Window control section
401 . . . Visual communication processing unit,
402 . . . Sound processing unit
403 . . . Window control section
501 . . . Graphics processing unit, 502 . . . Composer
503 . . . Sound processing unit, 504 . . . Window control section
501 . . . Video processing unit, 502 . . . Composer,
503 . . . Sound processing unit
504 . . . Window control section
901 . . . Video processing unit, 902 . . . Visual communication processing unit
903 . . . Graphics processing unit, 904 . . . Composer
905 . . . Sound processing unit, 906 . . . Window control section, 907 . . . Superimposition unit
1100 . . . Display, 1101 . . . Speaker unit
1101-1 and 1101-2 . . . Vibrator (actuator)
1102 . . . Stand
1200 . . . Operating room system, 1201 . . . Apparatus group
1203A to D . . . Display apparatus, 1205 . . . Recorder
1207 . . . Audio-visual controller (AC Controller)
1209 . . . Operating room control apparatus,
1283 . . . Patient bed
1287 . . . Ceiling camera, 1289 . . . Operating room camera, 1291 . . . Light
1700 . . . Vehicle control system,
17010 . . . Communication network
17100 . . . Drive system control unit, 17110 . . . Vehicle state detection section
17200 . . . Body system control unit, 17300 . . . Battery control unit
17310 . . . Secondary battery, 17400 . . . Vehicle exterior information detection unit
17410 . . . Imaging unit, 17420 . . . Vehicle exterior information detection section
17500 . . . Vehicle interior information detection unit, 17510 . . . Driver state detection section
17600 . . . Integrated control unit,
17610 . . . Microcomputer
17620 . . . General-purpose communication interface
17630 . . . Dedicated communication interface,
17640 . . . Positioning unit
17650 . . . Beacon reception unit, 17660 . . . Vehicle interior device interface
17670 . . . Sound image output unit
17680 . . . On-board network interface, 17690 . . . Storage unit

The invention claimed is:

1. An information processing apparatus comprising:
circuitry configured to
detect a position of a sound source appearing in a video displayed on a screen of a display, the sound source being placed in a plane of an image frame of the video; and
control one or more vibrators to vibrate the display, and thereby control output of sound such that a sound image of sound in synchronization with the video is localized at a position corresponding to the position, on the screen displaying the image frame of the video, of the sound source placed in the plane.

2. The information processing apparatus according to claim 1, wherein
the circuitry is configured to detect the sound source appearing in a video of broadcast or an OTT service or in an externally input video.

3. The information processing apparatus according to claim 1, wherein
the circuitry is configured to detect the sound source appearing in a video of visual communication.

4. The information processing apparatus according to claim 1, wherein
the circuitry is configured to detect, as the position of the sound source, a position of a graphic displayed on the screen and localize a sound image of sound related to the graphic.

5. The information processing apparatus according to claim 4, wherein
the circuitry is configured to detect, as the position of the graphic displayed on the screen, a position of a graphic of a sound agent executed on the information processing apparatus.

6. The information processing apparatus according to claim 5, further comprising:
a sensor configured to detect a user interacting with the sound agent, wherein
the circuitry is configured to control a display position of a character according to a position of the user.

7. The information processing apparatus according to claim 4, wherein
the circuitry is configured to detect, as the position of the graphic displayed on the screen, a position of a graphic of OSD or UI appearing on the screen and localize a sound image of a sound effect associated with the graphics in synchronization with display of the graphics on the screen.

8. The information processing apparatus according to claim 1, wherein, the circuitry is configured to, in a case of displaying videos of two or more video sources on individual windows, localize a sound image of a sound source detected from the video of each video source at a position corresponding to a position of the sound source appearing in the corresponding window.

9. An information processing method comprising:

detecting a position of a sound source appearing in a video displayed on a screen of a display, the sound source being placed in a plane of an image frame of the video; and using one or more vibrators to vibrate the display, and thereby control output of sound such that a sound image of sound in synchronization with the video is localized at a position corresponding to the position, on the screen displaying the image frame of the video, of the sound source placed in the plane.

10. A video sound output system comprising:

a display;

one or more vibrators configured to vibrate the display, and thereby output sound; and circuitry to detect a position of a sound source appearing in a video displayed on a screen of the display, the sound source being placed in a plane of an image frame of the video, and to control the output of sound such that a sound image of sound in synchronization with the video is localized at a position corresponding to the position, on the screen displaying the image frame of the video, of the sound source placed in the plane.

11. The information processing apparatus according to claim 1, wherein the plane is configured such that a video signal of the video is allocated thereto and is stored in a video memory.

12. The information processing apparatus according to claim 1, wherein the image frame of the video comprises a plurality of planes, and the circuitry is configured to place the sound source in one of the plurality of planes according to a type of the video including the sound source.

* * * * *